US005541062A

United States Patent [19]
Smeekens et al.

[11] Patent Number: 5,541,062
[45] Date of Patent: * Jul. 30, 1996

[54] METHODS AND COMPOSITIONS FOR PREPARING PROTEIN PROCESSING ENZYMES

[75] Inventors: Steven P. Smeekens; Donald F. Steiner, both of Chicago, Ill.

[73] Assignee: Arch Development Corporation, Chicago, Ill.

[*] Notice: The portion of the term of this patent subsequent to Jan. 14, 2011, has been disclaimed.

[21] Appl. No.: 98,756

[22] Filed: Jul. 28, 1993

Related U.S. Application Data

[63] Continuation of Ser. No. 484,074, Feb. 23, 1990, abandoned.
[51] Int. Cl.$^6$ .............................. C12Q 1/68; C12N 5/10; C12N 15/11; C07H 21/00
[52] U.S. Cl. .................... 435/6; 435/240.2; 435/320.1; 536/23.5
[58] Field of Search ........................ 435/6, 69.1, 320.1, 435/240.2; 536/23.5; 530/350

[56] References Cited

U.S. PATENT DOCUMENTS

| | | | |
|---|---|---|---|
| 4,650,763 | 3/1987 | Matsuo et al. | 435/224 |
| 4,704,359 | 11/1987 | Matsuo et al. | 435/69 |

FOREIGN PATENT DOCUMENTS

| | | |
|---|---|---|
| 0158981 | 4/1985 | European Pat. Off. . |
| 0246709 | 5/1987 | European Pat. Off. . |
| 0327377 | 2/1989 | European Pat. Off. . |
| WO88/08033 | 10/1988 | WIPO . |
| WO89/06279 | 7/1989 | WIPO . |

OTHER PUBLICATIONS

Ettinger et al., Biochemistry, 1987, 26, 7883–7892.
Lerman "Introduction." in: Lerman, *DNA Probes*, (New York, Cold Spring Harbor Laboratory, 1986), pp. 1–4.
Morrow "Recombinant DNA Techniques," in Methods in Enzymology, vol. 68, (Academic Press, 1979), pp. 3–24.
Matthews et al, Analytical Biochem, 169, p. 1–25 (1988).
Adams, T E, et al. "Non–Tolerance and Autoantibodies to a Transgenic Self Antigen Expressed in Pancreatic β Cells," Nature 325:223–228 (1987).
Andrews, P C, et al. "Precursors to Regulatory Peptides: Their Proteolytic Processing," Experimentia 43:784–790 (1987).
Brennan, S O, et al. "Calcium–Dependent KEX2–Like Protease Found in Hepatic Secretory Vesicles Converts Proalbumin to Albumin," 229:167–170 (1988).
Chan, S J, et al., "Cell–Free Synthesis of Rat Preproinsulins: Characterization and Partial Amino Acid Sequence Determination," Proc. Natl. Acad. Sci. USA 73:1964–1968 (1976).
Chick, W L, et al., "A Transplantable Insulinoma in the Rat," Proc. Natl. Acad. Sci. USA 74:628–632 (1977).

Davidson, H W, et al., "Intraorganellar Calcium and pH Control Proinsulin Cleavage in the Pancreatic β Cell Via Two Distinct Site–Specific Endopeptidases," Nature 333:93–96 (1988).
Fuller, R S, et al., "Yeast Prohormone Processing Enzyme (KEX2 Gene Product) is a $Ca^2$–Dependent Serine Protease," Proc. Natl. Acad. Sci. USA 86:1434–1438 (1989).
Fuller, R S, et al., "Intracellular Targeting and Structural Conservation of a Prohormone–Processing Endoprotease," Science 246:482–486 (1989).
Fuller, R S, et al., "Enzymes Required for Yeast Prohormone Processing," Ann. Rev. Physiol. 50:145–162 (1988).
Julius, D, et al., "Isolation of the Putative Structural Gene for the Lysine–Arginine–Cleaving Endopeptidase Required for Processing of Yeast Prepro–α–Factor," Cell 37:1075–1089 (1984).
Madsen, O D, et al., "Tissue–Specific Expression of Transfected Human Insulin Genes in Pluripotent Clonal Rat Insulinoma Lines Induced During Passage in vivo," Proc. Natl. Acad. Sci. USA 85:6652–6656 (1988).
Mizuno, K, et al., "Characterization of KEX2–Encoded Endopeptidase From Yeast *Saccharomyces Cerevisiae*," Biochem. Bioph. Res. Comm. 159:305–311, (1989).
Nishi, M, et al., "Conservation of the Sequence of Islet Amyloid Polypeptide in Five Mammals is Consistent with its Putative Role as an Islet Hormone," Proc. Natl. Acad. Sci. USA 86:5738–5742 (1989).
Oda, K, et al., "Putative Convertase Involved in the Proteolytic Conversion of Rat Proalbumin to Serum Albumin," J. Biochem. 104:159–161 (1988).
Roebrock, A J M, et al., "Evolutionary Conserved Close Linkage of the c–fes/fps Proto–Oncogene and Genetic Sequences Encoding a Receptor–Like Protein," The EMBO Journal 5:2197–2202 (1986).

(List continued on next page.)

*Primary Examiner*—George C. Elliott
*Attorney, Agent, or Firm*—Arnold White & Durkee

[57] ABSTRACT

The present invention relates to a new protein, convertin I, which belongs to a family of mammalian convertase proteins characterized by partial amino acid sequence homology to each of the following: the precursor processing endoprotease of yeast KEX2, bacterial subtilisins, and the human fur gene product, furin. The protein which is a subject of this invention is further characterized as a mammalian convertase, which is capable of hydrolytically cleaving, for example, prohormones to yield active hormones. Specifically, convertin I is capable of cleaving peptide bonds following certain sequences of two adjacent basic amino acids. Convertin I has a molecular weight of approximately 70 kd by electrophoresis. Another aspect of this invention is a recombinant vector, incorporating the coding sequences which are the objects of this invention. Methods of preparing the endoprotease protein, including molecular engineering methods are described. This invention also relates to a nucleic acid segment, including DNA and a cDNA having a sequence coding for convertin I. Methods of detection of said protein by, for example, fluorescent antibodies, and use of its coding sequences as hybridization probes are also provided.

16 Claims, 10 Drawing Sheets

OTHER PUBLICATIONS

Sevarino, K A, et al., "Amino–Terminal Sequences of Prosomatostatin Direct Intracellular Targeting but No Processing Specificity," Cell 57:11–19 (1989).

Steiner, D F, et al., "Intracellular Proteolytic Mechanisms in the Biosynthesis of Hormones and Peptide Nurotransmitters," Biochem. Clin. Asp. of Neur.: Syn., Proc., and Gene Struc. pp. 3–13 (1983).

Steiner, D F, et al., "Chemistry and Biosynthesis of Pancreatic Protein Hormones," Endocrinology 75:1263–1289 (1989).

Thim, L, et al., "Secretion and Processing of Insulin Precursors in Yeast," Proc. Natl. Acad. Sci. USA 83:6766–6770 (1986).

Thomas, G and Thorne, B A, "Gene Transfer Techniques to Study Neuropeptide Processing," Ann. Rev. Physiol. 50:323–330 (1988).

Wells, J A, et al., "Importance of Hydrogen–Bond Formation in Stabilizing the Transition State of Subtilisin," Phil Trans. R. Soc. Lond. 317:415–423 (1986).

```
                                                                                                                    10
                                                    Met Lys Gly Gly Cys Val Ser Gln Trp Lys
                                                    ATG AAG GGT GGT TGT GTC TCC CAG TGG AAG    117
                                                                                      40
Ala Ala Ala Gly Phe Leu Phe Cys Val Met Val Phe Ala Ser Ala Glu Arg Pro Val Phe Thr Asn His Lys Gly Gly Glu
GCG GCC GCC GGG TTC CTC TTC TGT GTC ATG GTT TTT GCA TCT GCT GAG CGA CCG GTC TTC ACG AAT CAT TTT GTG GAG GGA GAG    216
                        70
Asp Lys Ala Arg Gln Val Ala Ala Glu His Gly Val Arg Lys Leu Pro Phe Tyr His Phe Tyr His Asn Gly Leu Ala Lys
GAC AAA GCT CGC CAA GTT GCA GCA GAA CAC GGT GTT CGA AAG CTT CCC TTT TAT CAC TTC TAT CAC AAT GGC CTT GCA AAG    315
                                                  100
Ala Lys Arg Arg Ser Leu His His Lys Gln Leu Glu Arg Asp Pro Leu Met Ala Leu Gln Gln Glu Gly Phe Asp Arg Lys Lys Arg
GCC AAG AGA AGA AGC CTA CAC CAC AAG CAG CTG GAG AGG GAC CCC AGG GTA ATG GCT TTG CAG CAG GAA GGA TTT GAC CGA AAA AAG CGA    414
                                                                    130                                140
Gly Tyr Arg Asp Ile Asn Glu Ile Asp Ile Asn Met Asn Asp Pro Leu Phe Thr Lys Gln Phe Leu Ile Tyr Leu Gly Ile Asn Thr Gly Gln Ala Asp Gly Thr Pro
GGT TAC AGA GAT ATC AAT GAG ATC GAC ATC AAT ATG AAC GAT CCT CTT TTT ACA AAG CAG TTC CTG ATC AAT ACT GGA CAA GCT GAT GGC ACT CCT    513
                                                                                      170
Gly Leu Asp Leu Asn Val Ala Glu Ala Trp Glu Leu Gly Tyr Thr Gly Lys Gly Val Thr Ile Gly Ile Met Asp Asp Gly Ile Asp Tyr Leu His Pro
GGC CTT GAT TTG AAT GTG GCT GAA GCC TGG GAG CTG GGA TAC ACA GGT AAA GGT GTT ACC ATT GGA ATT ATG GAT GAT GGG ATT GAC TAT CTC CAC CCG    612
                                              190                                200
Asp Leu Ala Ser Asn Tyr Asn Ala Glu Ala Ser Tyr Asp Phe Ser Ser Asn Asp Pro Tyr Pro Tyr Pro Arg Tyr Thr Asp Trp Phe Asn Ser His His
GAC CTG GCC TCC AAC TAT AAT GCC GAA GCA AGT TAC GAC TTC AGC AGC AAC GAC CCT TAC CCC TAT CCA CGA TAC ACA GAT TGG TTT AAC AGC CAC    711
                                                                    230                                240
Gly Thr Arg Cys Ala Gly Glu Val Ser Ala Ala Ala Asn Asn Ile Cys Gly Val Gly Val Ala Tyr Asn Ser Lys Val Gly Val Ala Gly Ile Arg Met Leu
GGG ACC CGA TGT GCA GGA GAA GTT TCT GCT GCC AAC AAC AAT ATC TGT GGA GTT GGA GTA GCA TAC AAC TCC AAG GTT GGA GCT GGC ATC CGG ATG CTG    810

```
                                                                                                                                              1701
      510                    520                     530
His Val Gln Ala Val Ile Thr Val Asn Ala Thr Arg Arg Gly Asp Leu Asn Ile Asn Met Thr Ser Pro Met Gly Thr Lys Ser Ile Leu Leu Ser Arg
CAT GTC CAG GCT GTC ATC ACG GTC AAC GCA ACC AGA ACC AGA GAC CTG AAC ATC AAC ATG ACT TCC CCT ATG GGC ACC AAG TCC ATT TTG CTG AGC CGG
                540                                                560                                            570
                                                                                                                                              1800
Arg Pro Arg Asp Asp Lys Ser Val Gly Phe Asp Lys Trp Pro Met Thr Thr His Thr Phe Met Thr Thr Trp Gly Asp Ala Arg Gly Thr Trp Thr Leu Glu
CGT CCA AGG GAT GAC TCC AAG GTG GGC TTT GAC AAG TGG CCT ATG ACC ACT CAC ACG TTC ATG ACC ACC TGG GGA GAC GCC CGA GGC ACC TGG ACC CTG GAG
                                         580                                             590                                     600
                                                                                                                                              1899
Leu Gly Phe Val Gly Ser Ala Pro Gln Lys Gly Val Leu Lys Glu Trp Thr Leu Met Leu His Gly Thr Gln Ser Ala Pro Tyr Ile Asp Gln Val Val
CTG GGA TTT GTC GGC AGC GCC CCG CAG AAG GGG GTG CTG AAG GAG TGG ACC CTG ATG CTG CAT GGC ACT CAG AGT GCC CCG TAC ATC GAC CAG GTG GTG
                                 610                                              620                                    630
                                                                                                                                              1998
Arg Asp Tyr Gln Ser Lys Leu Ala Met Ser Lys Lys Glu Glu Leu Glu Glu Ala Val Glu Asp Ser Leu Arg Ser Leu Lys Asn Lys                          2127
CGG GAT TAC CAG TCC AAG TTG GCC ATG TCC AAG AAA GAG GAG CTG GAG GAA GCC GTG GAG GAC AGC CTG AGA AGC CTT AAC AAG
 638
Asn AM                                                                                                                                        2223
AAC TAG CCCTGCACATCCGCCTTCCCACCCCCCAGCTTCCCAACCTCCCGCTCCTCGTCCTCCAGTTCAGGCCAGGCCACCTAGCAATCCATCACCCGTACAGGCCAATTCGGTCTTCTTAATCTG
AAGCTTCACTCACTGTCAATGATTATTTCATTACAATGAAACAATCTTTTTACTCTATGCCCAAATATAGCGTTCCAACAACCCGGAATTC
```

| | | | |
|---|---|---|---|
| CONVERTIN: | ¹⁵⁷TGKGVTIGIMDDGIDYLHPDL.... | ¹⁹⁸PRYTDDWFNSHGTRCAGEVSA.... | ³⁷⁴GNCTLRHSGTSAAAPEAAGVF |
| Kex2: | ¹⁶⁵TGAGVVAAIVDDGLDYENEDL.... | ²⁰⁶PRLSDDY- - -HGTRCAGEIAA.... | ³⁷⁵GRCSNSHGGTSAAAPLAAGVY |
| ProprotB: | ¹⁶⁵AGRGVTSYDIDTGVNINHKDF.... | ¹⁹⁷LNDEDLDGNGHGTHCAGTIAS.... | ³⁵⁹DDATATLSGTSMASPHVAGLL |
| Sub BPN': | ²²TGSNVKVAVIDSGIDSSHPDL.... | ⁵⁴ETNPFQDNNSHGTHVAGTVAA.... | ²¹¹GNKYGAYNGTSMASPHVAGAA |

FIG. 6

```
PC2   MKG-GCVSQ----WKAAAGFLFCVMVFASAERPVFTNHFLVELHKGGEDKARQVAAEHGF--GVRKLP-----F      62
              ↳─────SP─────↲
KEX2  MKVRKYITLCFWWAFSTSALVSSQQIPLKDHT--SRQYFAVESNETLSRLEEMHPNWKYEHDVRGLPNHYVF      70
      ↳───────SP───────↲

PC2   AEGLYHFYHNG-----LAKAKRRRSLHHKQQLERDPRVK-MALQQEGFDRKKRGYRDINEIDINM|NDPLFTKQ    129
KEX2  SKELLKLGKRSSLEELQGDNNDHILSVHDLFPRNDLFKRLPVPAPPMDSSLLPVKEAED-KLSI|NDPLFERQ    141
                                                                     SD

PC2   WYLINTGQADGTPGLDLNVAEAWELGYTGKGVTIGIMDDGIDYLHPDLASNYNAEASYDFSSNDPYPYPRYT    201
KEX2  WHLVNP-----SFPGSDINVLDLWYNNITGAGVVAAIVDDGLDYENEDLKDNFCAEGSWDFNDNTNLPKPRLS   209
         *

PC2   DDWFNSHGTRCAGEVSAAANNNICGVGVAYNSKVAGIRMLDQPFMTDIIEASSISHMPQLIDIYSASWGPTD   273
KEX2  DDY----HGTRCAGEIAAKKGNNFCGVGVGYNAKISGIRILSGDITTED-EAASLIYGLDVNDIYSCSWGPAD   277

PC2   NGKTVDGPRELTLQAMADGVNKGRGGKGSIYVWASGDGGSY-DDCNCDGYASSMWTISINSAINDGRTALYD    344
KEX2  DGRHLQGPSDLVKKALVKGVTEGRDSKGAIYVFASGNGGTRGDNCNYDGYTNSIYSITIGAIDHKDLHPPYS    349
                                                  *

PC2   ESCSSTLASTFSNGRKRNPEAGVATTDLYGNCTLRHSGTS|AAAPEAAGVFALALEANLGLTWRDMQHLTVL|T   416
KEX2  EGCSAVMAVTYSSG---SGEYIHSSDINGRCSNSHGGTSAAAPLAAGVYTLLLEANPNLTWRDVQYLSIL|S   417
                                           SD
```

FIG. 7A

```
PC2   SKRNQLHDEVHQWRRNGVGLEFNHLFGYGVLDAGAMVKMAKDWKTV--PERFHCVGGSVQDPEKIPSTGKLV        486
KEX2  AVGLEKNADG-DWRDSAMGKKYSHRYGFGKIDAHKLIEMSKTWENVNAQTWFYLPTLYVSQSTNSTEETLES        488
PC2   LTLTTDACEGKENFVRYLEHVQAVITVNATRRGDLNINMTSPMGTKSILLSRRPRDDDSKVGFDKWPFMTTH        558
KEX2  VITISEKSLQDANFKR-IEHVTVTVDIDTEIRGTTTVDLISPAGIISNLGVVRPRDVSSE-GFKDWTFMSVA        558
PC2   TWGEDARGTWTLELGFVGSAPQKGVLKEWTLMLHGT------------------------------------        594
KEX2  HWGENGVGDWKIKVKTTENG-HRIDFHSWRLKLFGESIDSSKTETFVFGNDKEEVEPAATESTVSQYSASST        629
                                                                    ‾‾‾‾‾ST‾‾‾‾‾
PC2   ------------------------------------QSAPY------------------------------        599
KEX2  SISISATSTSSISIGVETSAIPQTTTASTDPDSDPNTPKKLSSPRQAMHYFLTIFLIGATFLVLYFMFFMKS        701
      ‾‾‾‾‾ST‾‾‾‾‾                                          ‾‾‾‾‾‾‾‾TM‾‾‾‾‾‾‾‾
PC2   ----------IDQVVRDYQSKL-----AMSKKEELEE---ELDEA---------VERSLKSIL         635
KEX2  RRRIRRSRAETYEFDIIDTDSEYDSTLDNGTSGITEPEEVEDFDFDLSDEDHLASLSSSENGDAEHTIDSVL        773
PC2   -NKN                                                                     638
KEX2  TNENPFSDPIKQKFPNDANAESASNKLQELQPDVPPSSGRS                                814
```

FIG. 7B ns# METHODS AND COMPOSITIONS FOR PREPARING PROTEIN PROCESSING ENZYMES

The U.S. government may own certain rights in the present invention pursuant to NIH grants DK13914 and DK20595.

This application is a Continuation of application Ser. No. 07/484,074, filed on Feb. 23, 1990, entitled METHODS AND COMPOSITIONS FOR PREPARING PROTEIN PROCESSING ENZYMES, abandoned.

BACKGROUND OF THE INVENTION

1. Field of the Invention

The field of this invention relates generally to proteins (convertases) which cleave precursor molecules in order to convert them to various active forms. Molecules which require such processing include hormone and neuropeptide precursors (neuromodulators). More specifically, this invention concerns a family of endoproteases structurally related to the following: kex2-endoprotease of yeast, bacterial subtilisins, and the human fur gene product, furin. Specifically, this invention relates to convertins, novel mammalian proteases and more specifically in this family convertin I. This invention is also related to the nucleic acids coding for this family of proteins, and to their complementary nucleic acid sequences. Methods of producing this family of proteins, for example, by use of human insulinoma derived cDNA or other methods of genetic engineering, are also provided. Applications and advantages of the protein family are presented, more specifically those of convertin I.

2. Description of Related Art
A. Maturation of Proteins

Although there are many kinds of regulatory peptides which differ in their function, cellular localization, and structure, they share a common property in that they are almost always initially synthesized in a larger form, that is, a precursor form, and subsequently are processed to form biologically active products. The first example of this processing was worked out for proinsulin, a larger precursor form of insulin, by Steiner, et al. (1976). The terminology developed by Steiner and colleagues to describe this phenomenon in terms of the intermediates produced during maturation, have been adapted to various intermediates produced during the biosynthesis of other regulatory peptides.

Regulatory peptides such as hormones and neuropeptides must undergo maturation processes to become biologically active, including proteolytic processing by various endoproteases. These endoproteases can cleave at various adjacent amino acid residues. As described in a review by Andrews et al. (1987), there are also enzymes involved in proteolytic cleavage to remove the hydrophobic signal peptide located at the amino terminus of the precursor. The "signal hypothesis" model of protein export from the cell was developed by Blobel and Dobberstein in 1975. Preproinsulin was demonstrated by Chan, et al. in 1976. An example of experiments which demonstrated the cleavage of the signal sequence are those of Minth, et al. (1984) using human pheochromocytoma, and those that isolated and characterized a 37 kd protease which is capable of cleaving the signal proteins of preproproteins from the honey bee prepromellitin, the human preproplacental lactogen, and preproinsulin. (Wickner, et al., 1985) This processing of "prepro-" forms of hormones and other secreted proteins occurs in the rough endoplasmic reticulum and results in removal of N-terminal segments of these proteins, depicted in FIG. I. There is subsequent cleavage of the "pro-" forms to release active products at single and double adjacent basic residues, followed by removal of the basic residues located at the C-terminus of the peptides by carboxypeptidase B-like enzymes. Proteolytic processing at dibasic amino acids represents an important step in the maturation of a large number of prohormones, neuropeptides, and other biologically active peptides and proteins.

While the synthesis of proteins which will eventually be secreted from the cell is usually initiated on cytoplasmic ribosomes, these very rapidly become tightly bound to the membrane of the endoplasmic reticulum across which the nascent peptide chain is transferred. Both eukaryotic and prokaryotic cells appear to use similar mechanisms for protein export. Bacterial cells can be used to export some eukaryotic proteins, and conversely, prohormones like proinsulin also can be processed by heterologous endocrine cells (Moore et al., 1983) and in distantly related eukaryotes such as yeast. (Thim et al., 1986). Bacteria can make, but do not cleave, prohormones, to yield the active forms.

B. Yeast Models

In the yeast, a eukaryote, precursors for at least two biologically active peptides have been identified: pro a factor and the prokiller toxin (see reviews in Mizuno et al., 1988; Andrews et al, 1987). Yeast cells exist which are defective in the proteolytic processing of precursors of these two proteins to a mature form e.g. KEX2 defective strains. The KEX2 gene encodes a novel endoprotease which is specific for cleaving these two precursor substrates on the carboxyl side of pairs of basic residues. The KEX2 gene has been cloned and introduced into multi-copy plasmids so that the protease is over-produced. From these cells, sufficient quantities of the endoprotease were obtained to allow purification to reportedly about 100 fold. The catalytic properties have been determined, indicating that the substrate site preferences of the kex2 endoprotease are on the carboxyl side of arginine-arginine (ArgArg) and lysine-arginine (LysArg). Enzyme activity is calcium dependent, similar to mammalian proteases called calpains, but they differ in catalytic mechanism in that kex2 is a serine protease. The complete amino acid sequence of the KEX2-encoded protein, deduced from nucleotide sequencing by Mizuno et al. (1988), revealed extensive homology between the amino acid sequences of the catalytic domain of the kex2 protein and those of the bacterial subtilisins (Section F). Sequence similarities around the active site residues resulting from similarities in gene structures (FIG. 2) suggest an evolutionary relationship between these proteases.

Matsuo et al. (1985, 1987) have patented a 43 kd serine-type protease prepared from *Saccharomyces cerevisae*. This enzyme hydrolytically cleaves peptide bonds between two adjacent basic amino acids, and in vitro, converts prohormones to active forms. (U.S. Pat. Nos. 4,650,763, 4,704, 1359, EP O158981A2). This enzyme was believed by the inventors to differ from that reported by Julius et al., (1984) (isolation of a gene (KEX2) encoding a yeast dibasic cleaving endoprotease). The inventors also claimed that the enzyme disclosed differed from the proteases reported by Fletcher et al., 1981; Loh et al., 1982; 1983; Mizuno et al., 1988. Cleavage was on the carboxyl side of repeating-X-Ala sequences, using enkephalin as a substrate. Subsequent work showed that kex2 showed no relation to this enzyme, as originally reported by Mizuno et al. in 1984 (Fuller, et al., 1988) and it is unlikely to be involved in precursor processing.

C. A Processing Enzyme in Fish

A protease has been identified from the anglerfish pancreatic islets by Fletcher, et al. (1981) and proposed to be one of the enzymes that processes proinsulin.

D. Mammalian Processing Enzymes

"The yeast KEX2 protease is the only enzyme that has a proven role in the activation of polypeptide hormones through cleavage at parts of basic residues. The enzyme that fulfills this role in higher eukaryotes has yet to be unequivocally identified," (Brennan and Peach, 1988) although various candidates have appeared on the scene, as discussed below.

An enzyme has been identified by Loh which converts mouse proopiomelanocortin to various products. This is a 70 kilodalton glycoprotein which has been purified from secretory vesicles of the bovine pituitary. However, it is unknown whether it functions in prohormone conversion in vivo. (Loh et al., 1987)

A prohormone converting enzyme which is found in rat microsomes and secretory granules has been described by Noe, et al. (1984) and said to be associated with membranes in the rat anterior pituitary neurointermediate lobe and rat hypothalamic synaptosomes. Noe suggested that the newly synthesized islet prohormones are membrane associated in the microsome and secretory granules and that the RER/Golgi complex and secretory granule membranes act as a matrix, uniting the enzyme and substrate. However, conclusive experimental evidence for this is lacking.

Davidson et al. (1988) reported the presence of two distinct Ca-dependent acidic endoproteases in lysates of secretory granules from a rat insulinoma. Type I cleaved on the C-terminal side of Arg 31, Arg 32 (B-chain/C peptide junction); type II, the C-terminal side of Lys 64, Arg 65 (C-peptide/A-chain function). Type II was postulated to also be active in the Golgi apparatus because of its more neutral pH optimum which allowed significant activity at pH 7.0 (the supposed pH of the Golgi). These results suggest that more than one processing enzyme may exist and this could be relevant to alternative processing. (Section E).

E. Complexities of Processing

Proteolytic processing of the same precursor molecule may occur in different ways, perhaps providing greater flexibility for the organism. The reasons for alternative processing are unclear and the systems are complex. The main physiologically active peptide produced as a result of proglucagon processing in the pancreas is the hormone glucagon. However, a larger peptide is derived from the C-terminal portion of proglucagon which has not yet been shown to possess biological activity. In contrast, in certain cells in the gut, four different physiologically active proteins are processed from proglucagon. Thus, there may be multiple recognition sites for different converting enzymes to produce different molecules from the same precursor.

On the other hand, some endoproteolytic enzymes, like kex2, seem to have low specificity and can recognize and cleave several precursor proteins, even those from unrelated eukaryote species. (Thomas and Thorne, 1988.)

F. Bacterial *Subtilisins*

Subtilisins belong to a serine protease superfamily. Bacteria of the bacilli species secrete at least two distinct levels of extracellular protease: a neutral metalloprotease, and an alkaline protease which is functionally a serine endopeptidase, "subtilisin." Secretion of these proteases has been linked to the bacterial growth cycle, with greatest expression of protease during the stationary phase when sporulation also occurs. (Joliffe, et al., 1980; Hastrup et al., 1989).

A wide variety of subtilisins have been identified, and the amino acid sequences of at least 8 have been determined. Some have been cloned. Subtilisins are well characterized physically and chemically. In addition to knowledge of the primary structure (the amino acid sequence), over 50 high resolution X-ray structures of subtilisin have been determined which delineate the binding of substrate, transition state products, different protease inhibitors, and structural consequences for natural variation. (Review in Hastrup, et al., 1989). Subtilisins have found utility in industry, particularly in detergent formulations, because they are useful for removing proteinaceous stains. Determination of the relationship between the primary structure of subtilisin and its physical properties have revealed the significance of the methionine 222 residue as well as the amino acids functional in the active site, that is, aspartic acid 32, histidine 64 and serine 221. Asparagine 155 and serine 221 are within the oxyanion binding site. Mutations of these positions are likely to diminish proteolytic activity. (Hastrup, et al., 1989). Desirable commercial characteristics of subtilisins produced by mutagenesis include improved stability to oxidation, increased proteolytic ability or improved washability (stability during commercial use).

G. The Fur Gene Product, Furin

"The fur gene was discovered fortuitously by comparing inserts of certain cosmid clones encoding the fes/fps oncogene with each other by means of Southern blot analysis." (Van de Ven et al., 1987). The furin protein is the fur gene product and is expressed in certain normal tissues, as well as in specific types of tumors, for example, non-small cell lung tumors, mammary and colon carcinomas, urogenital tumors and hematologic malignancies. Recombinant DNA carrying portions of the genetic information for furin has been produced and patented. In this patent antibodies against the furin protein for diagnostic use, were also described. (Van de Ven, et al., 1987). The N-terminal region of furin shares 50% amino acid-identity with the catalytic domain of kex2 protease. On this basis, Fuller, et al. (1989) have proposed that it is a candidate for a human prohormone-processing enzyme.

Despite years of searching for mammalian proprotein processing proteases that operate in vivo, these proteins have been elusive and the field has been confusing. The strategy employed by the inventors which is described in the following sections has led to success in identifying a mammalian protein, convertin, which shows partial homology to the catalytic modules of both kex2 and the related bacterial subtilisins, and also has similarities to furin.

SUMMARY

This invention is directed toward a nucleic acid segment containing a coding sequence for a protein, convertin I, which belongs to a family of covertin proteins, said family being characterized by amino acid sequence homology to each of the following: the precursor processing endoprotease of yeast KEX2, bacterial subtilisins, and the human gene product, furin. This protein was predicted to have an approximate molecular weight of 70 kd by its amino acid sequence. This was later confirmed by polyacrylamide gel electrophoresis (FIG. 3) and it is predicted to be an endoprotease from its sequence homology to other known endoproteases. The pH range of convertin I is expected to be 4–7 with an optimum at 5–6. The temperature range for activity is expected to be 22°–45° C., optimum 37° C. It will be inhibited by serine protease inhibitors, e.g., diisopropyl fluorophosphate.

This invention is also directed to a nucleic acid segment or its complement coding for a protein comprising approximately a 700 amino acid sequence substantially equivalent to that shown in FIG. 4, which contains as one embodiment, the active site comprising Asp, His and Ser residues. An embodiment with Asn instead of Asp at position 310, may be characterized by increased catalytic efficiency under some conditions. Those skilled in the art will realize that other amino acid substitutions may be made to alter or modify convertin activity without substantially affecting the basic structure of the protein. The nucleic acid segment referred to herein comprises approximately 1914 nucleotide pairs and is capable of hybridizing to the sequence of FIG. 4 or its complement. Various levels of stringent conditions will be desirable depending on the desired degree of homology, criteria well-known to those skilled in the art. A specific embodiment comprises a DNA segment.

This invention is also directed to a cDNA carrying the coding sequence for covertin. One method of obtaining covertin is from a human insulinoma from which the RNA templates were derived for amplification of catalytic-site conserved sequences for the DNA sequence coding for convertin 1.

What is also claimed is a protein which is coded by the nucleic acid segments referred to herein. One specific embodiment of this protein has a specific amino acid sequence which is in accordance with that shown in FIG. 4. It is a mammalian protein, a serine protease, the first such mammalian protein detected and characterized. It comprises a 282 residue domain that is homologous to the catalytic modules of both kex2 and the related bacterial subtilisins. 49% of the amino acids of the 282 residue domain are identical to those in the aligned kex2, and 27% are identical to the aligned subtilisin BPN' sequences respectively. The essential catalytic residues Asp, His and Ser are all conserved among these proteins. The convertin sequence is also greatly similar to the incomplete N-terminal sequence of the human furin gene product, a putative membrane inserted receptor-like molecule isolated from human tumors.

Generally, "convertin I" refers to a protein which is approximately 682 amino acids long, because this is the presently known approximate length. However, the invention does not preclude the preparation or use of shorter or longer peptides if these peptides have similar biological activities, structure, and cross-reactive immunologic reactivity, for example, as defined by guinea pig or rabbit polyclonal antisera. Moreover, biological activity may only require a peptide which includes the catalytic domain, approximately amino acid positions 122 to 415.

Covertin is further defined as comprising an amino acid sequence which is similar to that of subtilisin BPN', said similarity occurring at the Gly20 to Asp259 in subtilisin. The comparable sequence is Gly155 to Asp424 in the insulinoma-derived convertin I. A specific embodiment comprises a single open reading frame of 1914 bases coding for 638 residue amino acid sequences with an N-terminal cleavable signal peptide. As an endoprotease, convertin I has the capability of cleaving prohormones at dibasic amino acids to produce active hormones. An example of such a hormone would be insulin, which would be produced from the cleavage of proinsulin. Convertin I may also be defined as a prohormone convertase, more specifically a mammalian convertase. Similarly the cDNA coding for this protein is coding for a convertase. Homology of the new protein to the furin protein coded by the fur gene suggests that furin is a protease rather than a receptor as originally suggested.

Other aspects of this invention are recombinant vectors which incorporate the nucleic acid segments referred to above, or a biologically functional equivalent thereof. The recombinant vectors may also include RNA, cDNA, or a biologically functional equivalent thereof. In one embodiment, the nucleic acid segment included in the vector encodes amino acids and any segments found encoding the substilisin-like gene domain 122 to 415 essentially as set forth in FIG. 4. In another embodiment, the entire coding segment is contained in the vectors. Recombinant vectors and isolated segments may variously include the basic convertin I peptide codon region, said coding regions bearing selected alterations or modifications in the basic coding region, or larger proteins comprising the coding region. In addition, due to codon redundancy, this aspect of the invention is not limited to the particular sequences shown in FIG. 4.

For the recombinant vectors, the protein encoding sequence is positioned adjacent to, and under the control of, an effective promoter which can be adapted for expression in either a prokaryotic or a eukaryotic host. The recombinant vector may be used to produce cleavage of other proteins at specific sites in the same host, for example, in the commercial production of insulin, or may be used commercially to produce copies of the convertin I protein or a biological equivalent. On that basis, preparation of the convertin I protein or a biological equivalent protein as a product of the expression of a transformant prepared by genetic engineering techniques is well within the skills of those in the art.

Various eukaryotic vectors are well-known to those skilled in the art and may be used for insertion of the convertin I gene, e.g. RCD, RCMV, RMSG. Many host cell lines are available, e.g. AtT-20, RIN, MSLG2. (Chick, et al., 1977; Adams, et al., 1987; Sevarino, et al., 1989; Moore, et al., 1983; Madsen, et al. 1988).

It is a further object of this invention to describe methods of preparing the nucleic acid coding for convertin I, a specific embodiment comprises the steps of identifying and isolating nucleic acid from an insulinoma, preparing the cDNA by reverse transcriptase, using the polymerase chain reaction to detect and amplify the conserved sequences within the catalytic site coding sequence of the cDNA, followed by amplification of homologous DNA fragments, and fractionation and isolation of the amplified cDNA. A preferred insulinoma, as the source of RNA, comprises certain human insulinomas. Other insulin-producing cells and cells in which neuropeptides are processed, are also potential sources of convertin I. The inventors have used rat and mouse pancreatic and mouse brain cells as non-human sources.

A method is also described of forming a hormone from a precursor molecule by cleavage effected by the protein, convertin I. A method of converting a prohormone to an active hormone comprises hydrolytically cleaving said prohormone with a protease having the following properties: (1) hydrolytically cleaves peptide bonds between two specific adjacent amino acids; and (2) has a molecular weight of approximately 70 kd. Convertin I may also be used to cleave precursors of neuropeptides and other biologically active peptides and proteins, e.g., insulin, and/or insulin receptor precursors, as well as membrane glycoprotein precursors of various viruses, e.g., gp 160 of HIV-1 and others.

Antibodies may be specifically directed against convertin I by standard methods. These may be monoclonal antibodies or polyclonal antibodies. This protein may be identified in tissue or in vitro by use of fluorescent antibodies prepared against the protein.

Methods to prepare the nucleic acid segment substantially equivalent to the one coding for the convertin I, or a biological equivalent, comprise standard forms and methods. (Maniatis, et al. 1982). Short, hormonally active peptides, or short, nucleic acid fragments which hybridize to that essentially set forth in FIG. IV may be prepared as probes. The length is at least 14 bases, but may be larger. Nucleic acids are incubated with the appropriate segment under conditions appropriate for the formation of specific hybrids, and then those hybrids are detected with a label. The formation of such hybrids is indicative of the presence of complementary sequences.

The method of identifying specific nucleic acid sequences comprises incubating the sample with DNA or any nucleic acid segment under conditions appropriate for the formation of specific hybrids and then detecting the presence of such hybrids by means of a label, either before or after amplification of the DNA by means of PCR or related methodologies. (Mullis, 1987).

One application of these methods is to screen clone banks. This new endoprotease may also be used for applications characteristic of proteolytic enzymes. However, it will be specifically useful to cleave proproteins in host cells into which the proproteins have been transferred by methods of genetic engineering. There are advantages of using a natural mammalian preprocessing enzyme in commercial production of hormones, instead of an artificial non-mammalian one. The hormone is more likely to emerge as it does in its natural structure, and there are less undesirable byproducts than there are using, e.g., trypsin.

The following terms are used herein:

Substantially purified is used herein to refer to DNA segments isolated free of their natural state, as they might be present in the genome of an organism. This term is intended to include such segments as they would exist upon genetic engineering, for example, for insertion into a recombinant vector.

The term complementary used herein in connection with amino acid sequences, refers to amino acids or peptides that exhibit an attractive force toward each other. With respect to nucleic acid sequences, the term complementary refers to sequences having sufficient complementarity to allow specific cross-hybridization of nucleic acid strands.

Biologically functional equivalent functionally significant homology requires similarity in function, e.g. catalysis, as well as a minimum of 40–60% amino acid sequence identity in important regions, for example, as found among related trypsins. The identity criteria could in some instances be satisfied by amino acid equivalents (Table I). This phenomenon enables a wide range of equivalent embodiments to be prepared from the disclosures herein.

As used herein, the phrase biologically functional equivalent, referring to amino acids, refers to the fact that the invention contemplates that changes may be made in certain of the foregoing basic sequences without necessarily reducing or losing their proteolytic or structural identity. For example, the sequence can be altered through considerations based on similarity and charge, for example, acidity or basicity of the amino acid group, hydropathic index or amphipathic score. In general, these broader aspects of the invention are founded on the foregoing general understanding in the art, that certain amino acids may be substituted for other like amino acids without appreciable loss of the peptide's ability to bind and to be active. Examples of exemplary embodiments of amino acids and substitutions are shown in Table I. The same expansion of nucleic acid sequences is within the scope of this invention. The sequence of FIG. IV can be altered by making these substitutions, additions or deletions to provide for functionally equivalent molecules. For example, due to the degeneracy of nucleotide coding sequences, other DNA sequences which encode substantially the same amino acid sequence as depicted in Table I may be used in the practice of the present invention. One or more amino acid residues within the sequence can be substituted by another amino acid of a similar polarity which acts as a functional equivalent. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic and glutamic acid.

Closeness of relation can be measured by comparison of amino-acid sequences. There are many methods of aligning protein sequences, but the differences are only manifest when the degree of relatedness is quite small. The methods described in the Atlas of Protein Sequence and Structure, entitled SEARCH and ALIGN, define relatedness. As is well known in the art, related proteins can differ in number of amino acids as well as identity of each amino acid along the chain. That is, there can be deletions or insertions when two structures are aligned for maximum identity.

TABLE I

| Original Residue | Exemplary Substitutions |
| --- | --- |
| Ala | Gly; Ser |
| Arg | Lys |
| Asn | Gln; His |
| Asp | Glu; Asn |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr; Phe |
| Tyr | Trp; Phe |
| Val | Ile; Leu |

Because of the nucleic acid code degeneracy, which means that more than 1 codon will code for a particular amino acid, a collection of nucleotide sequences representing all possible codon variations of FIG. 4 are within the scope of this invention. The sequence illustrated in FIG. 4, and its complement, is a specific embodiment.

Other definitions and terms used in this invention include:

Proteases (peptidases) are enzymes which cleave the amide linkages in protein substrates.

A serine protease is an enzyme which catalyzes the hydrolysis of peptide bonds in which there is an essential serine residue at the active site.

A vector is a genetic element (a "replicon") to which other DNA segments may be attached, thereby bringing about replication of the attached segment. Examples include: plasmids, cosmids, chromosomes, viruses. Coding sequence refers to a nucleotide sequence that is transcribed (DNA-RNA) and translated (RNA-protein) into a polypeptide, either in vivo or in vitro.

Transcription, initiation, and termination sequences regulate DNA. They flank a coding sequence. Promoter sequences are initiators.

Substantial homology is said to occur when: 1) one amino acid sequence predicts a structure fundamentally similar and thereby generally biologically equivalent to another; 2) nucleotides coding for the amino acid sequence match over a defined length of the protein molecules (at least 60% or more). Sequences that are substantially homologous can be identified under conditions of a selected stringency. Defining appropriate hybridization conditions is within the skill of the art. (Maniatis, et al. 1982.)

A processing site refers to codons defining the minimum number of amino acid residues specifically required for cleavage by a selected process.

An open reading frame is a series of codons without termination codons; the sequence is potentially translatable into proteins.

Conservative residues are "exemplary substitutes" as in Table I, i.e., chemically similar residues.

Consensus sequences are those that are similar from related members of a family.

BRIEF DESCRIPTION OF THE DRAWINGS

Other objects and advantages of the invention will become apparent upon reading the following detailed description and upon reference to the drawings in which:

FIG. 4A, FIG. 4B and FIG. 4C. Nucleotide and predicted amino acid sequences of convertin I. The number of the nucleotides is indicated at the end of each line. The arrow indicates the putative cleavage site of the signal peptide. The proposed active site ASP, HIS, and SER residues are boxed. Solid bars indicate consensus sequences for N-linked glycosylation. (This nucleotide sequence has been submitted to the GenBank™ EMBL Data Bank with accession number(s) J05252.)

FIG. 5. Conservation of active site residues between KEX2 and furin. Active site Asp, His, Asn, and Ser residues found in the subtilisin family of serine proteases are indicated by arrows. Boxed residues are conserved in all sequences. Triangles indicate positions at which KEX2 and furin are identical and deviate from all the other subtilisin family members. Underlined residues are conserved between KEX2 and at least one other sequence. Prbl, *S. cerevisiae* vacuolar proteinase B; Prok, *Tritirachium album Limber* proteinase K; Ther, *Thermoactinoymces vulgaris* thermitase; Subt(1), *Bacillus subtilis* subtilisin Carlsberg; Subt(2), *B. subtilis* subtilisin DY; Subt(3), *B. amyloiquefaciens*, subtilisin BPN'; Subt(4), *B. subtilis* var. *amylosaccharificus* subtilisin S; and Subt(5), intracellular subtilisin from *B. subtilis* A-50 (Fuller, et al., 1989).

FIG. 6. Comparison of selected regions of convertin I to the amino acid sequences surrounding the active site catalytic residues of KEX2 proprotease B, and subtilisin BPN'. The relative position of the amino acid segment within each of the proteins is indicated by the numbers to the left of each column. Residues identical to those of convertin I are boxed. Catalytic residues are indicated by an asterisk. Amino acids are indicated by their single-letter abbreviations.

FIG. 7A and FIG. 7B. Comparison of the amino acid sequences and catalytic domain structures of convertin I and KEX2. The positions of the signal peptides (SP), subtilisin-like domains (SD), Ser/Thr-rich domain (ST), and transmembrane spanning region (TM) are indicated. Amino acids are indicated by their single-letter abbreviations. The number of the amino acids is indicated at the end of each line. A colon represents identical amino acids, and a period represents chemically similar residues. Gaps introduced into the alignment are indicated by hyphens. Active site catalytic residues are indicated by an asterisk.

DESCRIPTION OF THE PREFERRED EMBODIMENT

"Many bioactive peptides are processed from their precursors by proteolytic cleavage at paired basic residues. However, little is known about the endopeptidases that are physiologically involved in precursor processing." (Mizuno et al., 1988; citing Docherty and Steiner, 1982).

Figure 1:
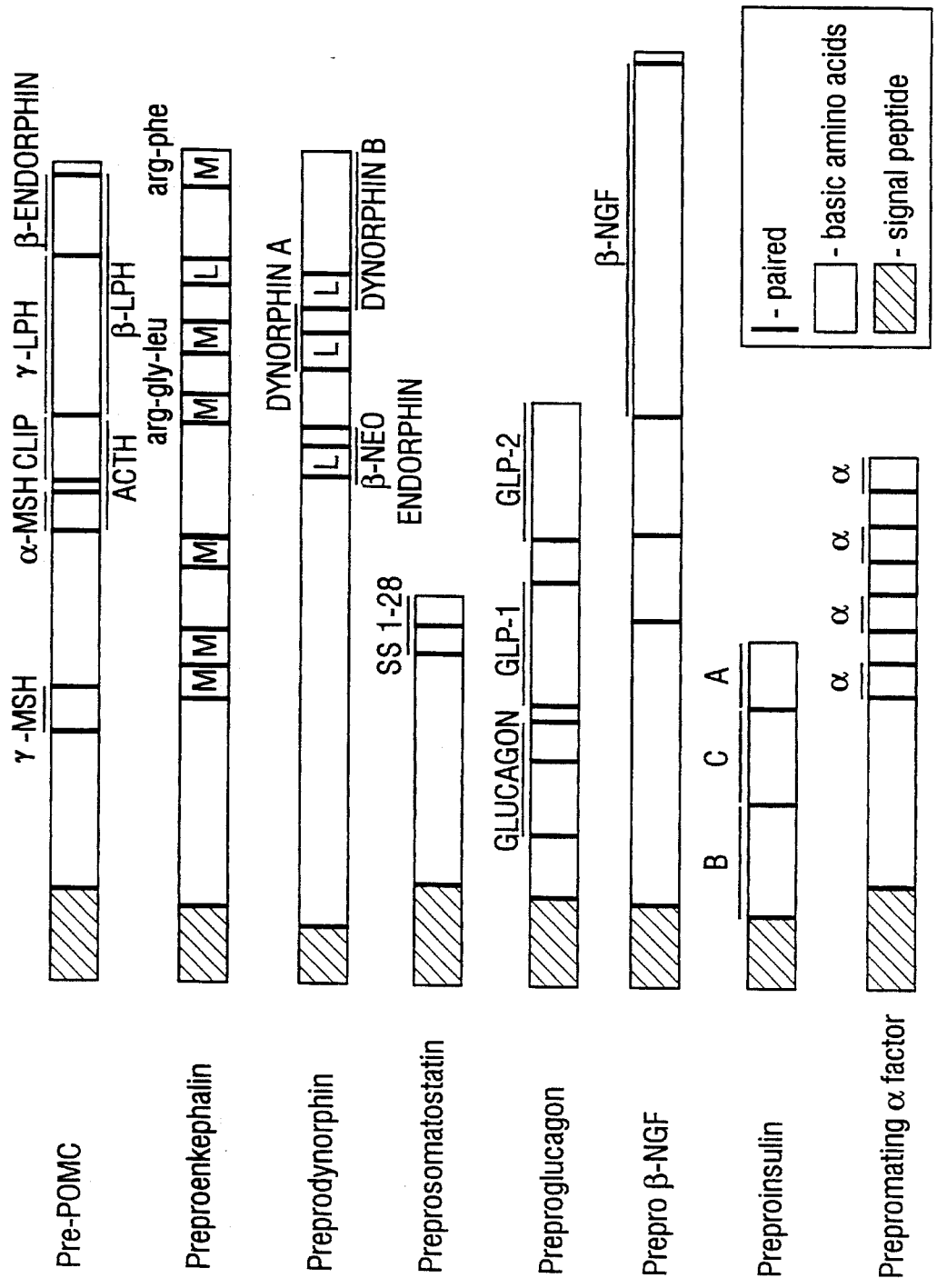
FIG. 1. Schematic diagram of structures of some of the known proproteins showing residues at cleavage sites. Heavy single lines indicate regions which appear as biologically active products. (Steiner et al. 1983).
Figure 2:
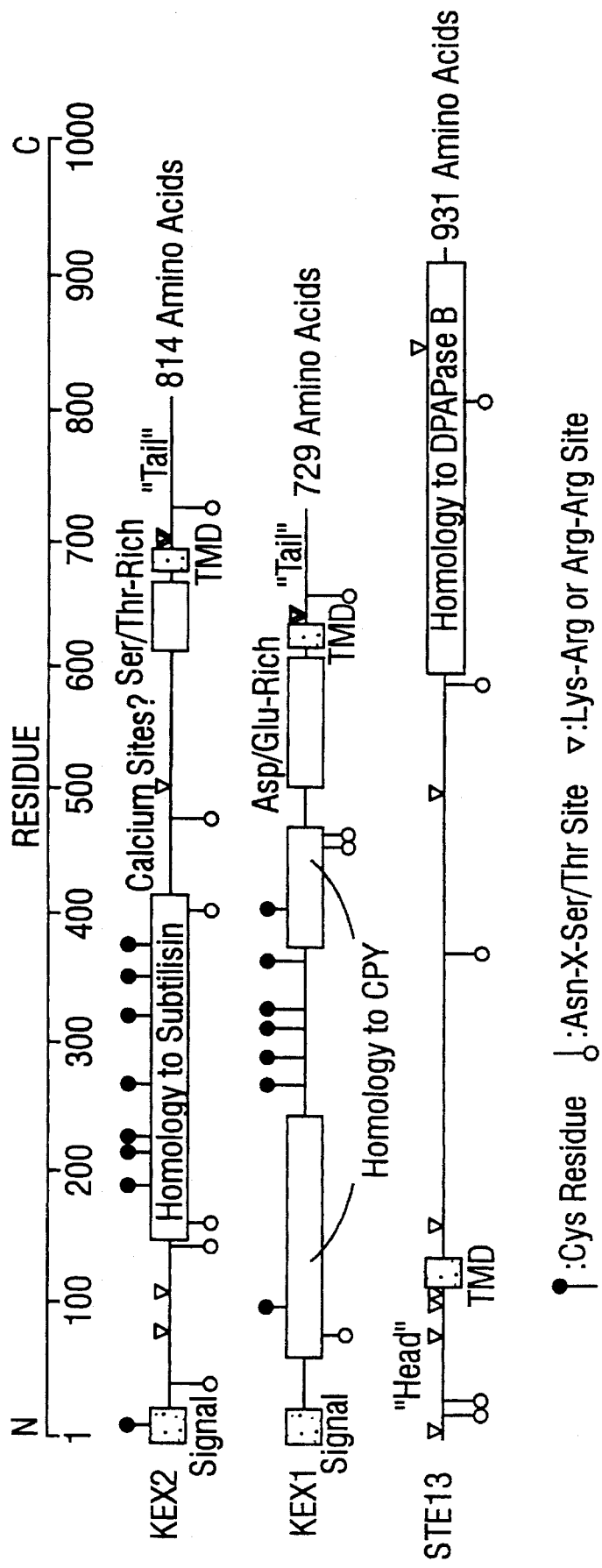
FIG. 2. Schematic depiction of predicted amino acid sequences of yeast precursor processing enzymes. The deduced amino acid sequences, homologies to known proteases, and inferred structural features are derived from the nucleotide sequences of the cloned structural genes, KEX2, KEX1, and STE13. (Fuller et al., 1988).

Small peptide hormones and neuromodulators are usually synthesized initially as large precursor proteins (FIG. 1) that undergo tissue specific post-translational modifications and proteolytic cleavage to produce mature bioactive peptides. Cleavage may occur at the N-side, C-side or the middle of adjacent two basic amino acids. The peptides in the precursor protein are typically flanked by pairs of basic amino acids, for example lysine-arginine or lysine-lysine. Maturation of the bioactive peptide is generally a two step process. The pair of basic amino acids is cleaved by a trypsin-like endopeptidase and then the remaining flanking amino acids are removed by a carboxyl peptidase B-like enzyme or a similar amino peptidase before being released from the cell. The mature peptide may undergo a further series of modification reactions, for example, N-terminal acetylation or C-terminal amidation.

Thomas and Thorne, 1988.

Although some information on proprocessing systems has accrued from studies of prokaryotes, "The authentication of mammalian neuroendocrine protein processing endopeptidases has proven a formidable task." (Thomas and Thorne, p. 329.)

The paired basic residues which are the site of proteolytic processing of various bioactive peptide precursors appear in a wide range of eukaryotic species ranging from yeast to mammals. The discovery of calcium dependent endopeptidases which convert proinsulin and proalbumin to their mature products were reported by Davidson, et al. (1988), Brennan, et al. (1988) and Oda, et al. (1988). It was not clear from these studies whether these enzymes could be classified into a serine protease family, although Brennan and Peach (1988) raised the possibility that "a family of $Ca^2$ dependent proteases may be involved in the processing of the mammalian proproteins." (p. 170) There were some overlapping properties, specifically membrane association, substrate specificity, calcium dependency, and acidic pH optimum. These properties were shared by the KEX2 endopeptidase described in detail by Mizuno, et al., 1988. It had been demonstrated that the yeast KEX2 protein gene product expressed in mammalian cells was correctly able to process proinsulin expressed in yeast (Thim, et al., 1986), and proopiomelanocortin when transfected into mammalian cells. (Thomas, et al., 1988). These facts suggested that endopeptidases with properties similar to kex2 might be involved in precursor processing in mammalian tissues.

A serine protease is an enzyme in which there is an essential serine residue at the active site which catalyzes the hydrolysis of peptide bonds. (White, Handler and Smith, 1973). The trypsin-like serine proteases have molecular weights in the 25,000–30,000d range. They hydrolyze simple terminal esters and are similar in activity to eukaryotic chymotrypsin, also a serine protease. The alternative term, alkaline protease, reflects the high pH optimum of the serine proteases ranging from pH 8.0 to 10.0.

Table II illustrates the relationships among various serine proteases.

residues are the crucial tests, however, for membership and classification in the serine proteases.

Serine proteases are a diverse class of enzymes having a wide range of specificities and biological function. (Stroud 1974). Despite their functional diversity, the catalytic machinery of serine proteases in at least two genetically distinct families of enzymes: the *Bacillus* subtilisins and the mammalian and homologous bacterial serine proteases (for example, trypsin and *S. gresius* trypsin), show remarkably similar mechanisms of catalysis. (Kraut 1977). Furthermore, although the primary structure is unrelated, the tertiary structure of these two enzyme families brings together a conserved catalytic triad of amino acids, consisting of Ser, His and an Asp. These residues are positioned to facilitate nucleophilic attack by the serine hydroxylate on the carbonyl of the scissile peptide bond.

Andrews, et al. (1987) have reviewed examples in humans which illustrate the necessity of cleavage at two adjacent basic amino acid residues to effectively preprocess some precursors. However, "The mammalian enzyme which recognizes and cleaves the prohormone at the two basic residues has not been isolated in pure form, nor characterized." (Andrews, et al., 1987) The two basic residues usually comprise arginine (Arg), preferentially adjacent to lysine (Lys). The first example is families with hyper-insulinemia. Normally proinsulin is cleaved following the Arg of an ArgGly peptide bond which connects the C-peptide and the A-chain of proinsulin on the carboxyl side of the ArgGly. A point mutation identified in humans in the arginine 65 codon changes the Arg residue to His, resulting in blockage of the

TABLE II

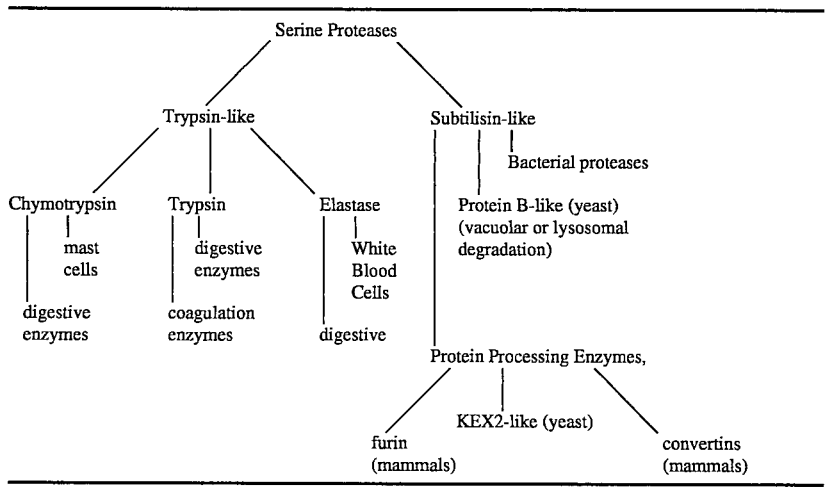

The branches of subtilisin-like proteases are likely to become more complex as related mammalian members are discovered and characterized.

Differences among serine proteases would include an arrangement of catalytic residues, e.g., in both trypsin and subtilisin serine proteases, Asp, His, and Ser are the amino acids of the catalytic triad. However, in trypsin-like serine proteases, they are arranged in the sequence His, Asp, Ser, whereas in subtilisin-like proteases are arranged as Asp, His, Set. There are also differences in the relative spacing of these key residues. In addition, there are other evolutionarily conserved features of these proteases which allow them to be identified as serine proteases and subsequently classified. The presence of the catalytically important Asp, His, and Ser post-translational cleavage of proinsulin to insulin, because that bond (HisGly) cannot be cleaved.

A second example is in the processing of proalbumin, wherein alterations in the amino acid sequence of proalbumin result in variants which cannot convert to albumin by processing after two adjacent Arg residues. In one of the variants, the alteration results in yielding an ArgGlu substitution, whereas in another there is a HisArg substitution which resists cleavage. These changes both lead to persistence of the unprocessed proalbumin.

A third example is a variant of Factor IX (Factor IX Cambridge) coagulant activity resulting in the clinical condition of hemophilia B. In this variant, there is a LysSer substitution for the normally observed post translational processing site, LysArg. This point mutation impairs proteolytic processing and results in the disease hemophilia B. Clearly, as these examples illustrate proper conversion and processing of propeptides into the active protein forms is crucial for normal development and functioning of the organism.

A number of precursor proteins contain sequences of more than one bioactive peptide, for example, the opioid peptides. In this example, three precursor proteins are responsible for the generation of 16 products. Different peptides resulting from a single precursor exhibit tissue specificity. Experiments designed to study the mechanisms of tissue specificity include transfecting the specific genes of interest into genomes of heterologous cell types. These methods have been used to examine the proteolytic maturation of proinsulin, pro-enkephalin, proglucagon and prosomatostatin by stable gene transfection.

1. The Yeast kex2 Endopeptidase

The yeast KEX2 gene encodes an endopeptidase which has homology to subtilisin-like serine proteases. Mizuno, et al. have characterized the amino acid sequence of the KEX2 gene product deduced from nucleotide sequences. They have found that the KEX2 gene contains a 2,442 base pair open reading frame encoding a polypeptide of 814 amino acids. The deduced amino acid sequence contains a region homologous to the subtilisin-like serine protease family near the N terminus. A putative membrane spanning domain near the C-terminus was also reported, suggesting that KEX2 encoded protein may function as a membrane bound subtilisin-like serine protease. (Julius et al., 1984; Mizuno et al., 1988, 1989; Fuller et al, 1989.) Yeast cells comprise both an alpha factor and killer toxin which require processing from larger precursors by cleavage at paired basic residues. Information on the yeast model system has provided information on proteolytic processing in higher eukaryotes. The KEX2 gene product shows membrane association, is calcium dependent, and has substrate specificity toward paired basic residues. The KEX2 gene was first isolated by Julius, et al. (1984).

Further indications that the yeast kex2 enzyme is an appropriate model for studies of human convertases, enzymes that cleave precursors to yield active proteins, is indicated by the fact that kex2 processes normal human proalbumin, but not proalbumin Christchurch, which does not have the appropriate cleavage site. Furthermore, this yeast enzyme is inhibited by α-1- antitrypsin Pittsburgh which attacks the basic site for the cleaving enzyme, but is not inhibited by normal α-1- antitrypsin. Kex2 has also been shown to process proinsulin expressed in yeast (Thim, et al., 1986) and also to process pro-opiomelanocortin when transfected into POMC secreting mammalian cells. (Thomas and Thorne, 1988)

The major components of the kex2 protein are: 1) a signal sequence; 2) a domain homologous to the catalytic site of bacterial subtilisins; 3) a Ser and Thr rich region; and 4) a transmembrance spanning domain. There is evidence suggesting that proper cellular localization of kex2 is necessary for maximum biological function. (Fuller, et al. 1989).

By studying the endonuclease kex2, which is overproduced in yeast, Fuller determined that the characteristics of this protein were: 1) membrane bound, but solubilized by detergents: 2) able to cleave peptide substrates at both LysArg and Arg-Arg sites, 3) inhibited by EDTA and EGTA but not by phenanthroline, but fully reactivated by calcium: 4) unaffected by 5–10 mM phenylmethylsulfonyl fluoride, Nαα(α-tosyl) lysine chloromethyl ketone but inactivated by 1–2 mM Ala Lys Arg-chloromethyl ketone; 5) labelled specifically by $^{125}$I-labelled Tyr Ala Lys Arg-chloromethyl ketone and 6) resistant to transepoxysuccinate compounds which inhibit thiol proteases, but inactivated by diisopropyl fluorophosphate, a diagnostic serine protease inhibitor. Unlike subtilisins, inhibition of kex2 protease by chelators was freely reversible. Thim, et al., (1986) determined that a spacer peptide was required for processing of the insulin precursor molecule. This was done by examining the results of recombinant plasmids constructed to encode fusion proteins with modified mating factors and insulin precursors in yeast. These investigators proposed that in hormone precursors in general, the spacer peptides serve to expose dibasic sequences for processing.

2. Bacterial Subtilisins

The term subtilisin designates a group of extra-cellular alkaline serine proteases produced by various species of bacilli. These enzymes are also referred to as bacillus serine proteases, bacilli subtilisins, or bacterial alkaline proteases. The subtilisin type BPN' produced by Amyloliquefaciens is one of the groups of subtilisin molecules and contains 275 residues. X-ray structure of subtilisin BPN' revealed that the geometry of the catalytic site of subtilisin involving Asp 32, His 64 and Ser 221 is almost identical to that of the active site of mammalian serine proteases for example chymotrypsin (Asp 102, His 57 and Ser 195). However, the overall dissimilarities between bacilli serine proteases and mammalian serine proteases indicate these are two unrelated families of proteolytic enzymes. There is extensive homology between amino acid sequences of subtilisins from different strains of bacillus. In the major commercial uses of subtilisins for detergents, enzyme instability under washing conditions is a limiting factor. There is a continuing search for subtilisin analogs with improved pH and thermal stability rendering them especially useful for detergent formulations as well as for other processes requiring stable proteases. An example of such a modification is presented by Zurowski, et al., 1988.

3. Human Tumor Furin Protein

It was deduced from comparisons of characteristics of furin with those of the human insulin receptor and the human epidermal growth factor receptor, that fur may encode a "membrane-associated protein with a recognition function." (Roebroek et al. 1986).

The fur gene is found in both the human and the cat genome upstream of the fes/fps protooncogene. Computer analysis by Roebroek, et al. (1986) indicated that the furin gene product maintains a possible transmembrane domain similar to that of Class II MHC antigen. There was also a cysteine rich region which was homologous with cysteine rich regions of the human insulin receptor and the human epidermal growth factor receptor. This homology extended over a stretch of 135 amino acid residues.

The furin transcription unit appears to be distributed over a DNA area of about a 10 kb length. The amino acid sequence derived from the open reading frame of about 1500 nucleotides contains a hydrophobic region similar to that found in transmembrane domains. This hydrophobic region is approximately 50 amino acid residues upstream of the carboxyl terminus. Expression of the fur gene as examined by Northern blot analysis, showed variation of expression in different tissues. There was also an increase in malignant tissues compared to normal tissues of the same source, for example, lung samples. The results of Van de Ven indicated that the fur gene could be a suitable tumor marker for distinguishing between tumor types; elevated expression was found in the non-small cell lung carcinoma as opposed to the small cell lung carcinoma which were compatible with normal lung tissue levels. In man and cat, the linkage of the fur and fes/fps transcription units has been conserved during evolution. This may indicate there are functional needs for this region which may lead to information on the regulation of the expression of the c-proto-oncogene, implicated in the paths of carcinogenesis. Similarities of furin with the catalytic domain of the KEX2 protease led Fuller, et al. (1989) to suggest a role for furin in human prohormone processing.

4. Difficulties in Isolating and Characterizing Mammalian Processing Enzymes

It has been very difficult to isolate processing proteases from mammalian cells because the processing enzymes are merged in the separation methods with other proteases found in lysozymes. Consequently it is difficult to separate them. No mammalian enzyme which converts prohormones to active forms in vivo has been identified, isolated and characterized. Many candidates have been alluded to, but little is known about them.

As remarked by Thomas "the authentication of mammalian neuroendocrine protein processing endopeptidases has proved a formidable task." Several candidate processing activities have been characterized, but as yet not one has been convincingly demonstrated to be a bona fide processing enzyme. Some of the problems arise from difficulties in manipulating the phenotype of mammalian cells as opposed to yeast, which are amenable to these manipulations. Another problem has been that only extremely small amounts of precursor protein can be isolated from tissue preparations. This problem has been somewhat alleviated by use of CD and As clones which produce a number of precursor proteins. It is now possible to express high levels of these proteins. Various vectors used for this purpose are discussed in Thomas and Thorne (1988).

According to Julius, et al., (1983) three problems have plagued attempts to identify specific proteases responsible for precursor processing in animal cells. 1) it is difficult to separate the population of secretory cells in a tissue and it is difficult to prepare appropriate sub-cellular fractions from these cells; 2) there is relatively low level of activities in the sub-cellular fractions; and 3) there is a high level of presence of several other enzymes of similar specificity resulting from unavoidable contamination by lysosomal material. Yeast has been a model system providing a uniform population of secretory cells; also yeast has an advantage that the major proteolytic activities are well described, mutants are available, and yeast genes carried by multi-copy plasmids overproduce their protein products. These advantages are responsible for the success in cloning and characterizing the KEX2 gene product. (Julius, et al., 1984). These problems have not been solved for mammalian systems prior to the work described in this invention.

5. Techniques of Molecular Biology to Produce and Analyze Proprotein Processing Enzymes Recombinant SV40 virus has been used to express proinsulin and growth hormone in Simian cells. (see Review in Thomas et al., 1988). However, this system is not efficient for expression in mammalian cells.

Some of the problems in recombinant proteins produced in bacteria are that bacteria may not correctly modify the proteins. In mammalian cell systems the level of recombinant protein expression is much lower than that observed from bacterial systems. There are disadvantages, therefore, in both systems.

One transient expression system makes use of the COS cell line. Neuroendocrine genes and cDNA'a which have been expressed using this system include rat and human preproinsulin, anglerfish preprosomatostatin, and porcine proopiomelanocortin. (Thomas et al., 1988). No processing of prohormones occurs in this system. Introduction of convertins might correct this.

Vaccinia virus can accommodate large and or multiple foreign inserts. Because cDNA's have been cloned for a number of precursor proteins, it is now possible to express high levels of each precursor. A variety of vector systems have been used for this purpose including vaccinia and could be used to express convertins. Inherent shortcomings of gene transfer studies are that the molecular mechanisms that govern the processing of neuroendocrine precursor protein in heterologous cells may differ from those present in homologous cells. To overcome this problem, germ line transmission using SV40T and rat proinsulin promoter may be performed. Transfer into the germ line of mice will result in specific formation of pancreatic β-cell tumors will produce insulin and may be suitable for expressing convertins.

6. The Present Invention

As discussed in previous sections, proteolytic processing at dibasic amino acids represents an important step in the maturation of a large number of prohormones, neuropeptides, and other biologically active proteins. Despite the widespread occurrence of this mechanism in nature, little is known about the endoproteases involved in this process. The yeast KEX2 protease is the only enzyme that has a demonstrated role in the activation of polypeptide hormones by means of cleavage sites at pairs of basic residues. (Fuller et al. 1988; Brennan and Peach, 1988). As these authors point out, an enzyme of comparable function has not been identified for higher eukaryotes. A new enzyme identified by Brennan, et al. was found in rat hepatic microsomes. Enzyme characteristics were as follows: it was KEX2-like in that it was calcium dependent, membrane bound, and had a pH optimum of 5.5–6.0 (see Fuller et al. 1989). Its function was to convert proalbumin to albumin.

It had been suspected from examination of the activity of the KEX2 gene in yeast and from the observation that the kex2 protease had the ability to process some purified human proteins, that this protease might be the prototype for mammalian enzymes. However, there was no answer to the question, ". . . just how similar are the yeast and mammalian processing enzymes and the reaction catalyzed?" (Fuller, et al. 1988; Orci, et al. 1985). KEX2 was believed to function in the yeast Golgi. In contrast the newly formed secretory granules may be the site of most mammalian proprotein processing, e.g., of proinsulin.

Several mutations in humans that block proalbumin processing have led to elucidation of proposed mechanisms of cleavage at the basic site. Analysis of these mutations indicates that a specific peptide is cleaved from proalbumin just before its secretion from the hepatocyte. The existence and characteristics of various circulating variants, namely proalbumin (Christchurch), proalbumin Lile and proalbumin Takefu, have established the requirement for a pair of basic residues at the cleavage site.

As soon as KEX2 was found, researchers searched for possible analogues in higher life forms, but none were found. One usual method of searching was to use KEX2 cDNA to screen libraries, a strategy that had been successful in detecting analogues for CD2 and the ras oncogene in higher life forms. This method was not, however, successful in detecting a KEX2 like protein in higher life forms. As described herein, a new strategy developed by the inventors was successful is in isolating a mammalian protein, convertin I. This strategy was to amplify homologous DNA fragments (Nishi, et al., 1989), using polymerase chain reaction (PCR) to detect and amplify conserved sequences within the catalytic site of KEX2. The source of cDNA was a human insulinoma. This cDNA was found to encode a protein, convertin I, which is homologous to the precursor processing KEX2 endoprotease of yeast. Based on its sequence homologies, convertin I is a member of a family of mammalian KEX2/substilisin-like proteases (Table II) that includes members involved in a number of specific proteolytic events within cells, including the processing of prohormones.

Figure 3:
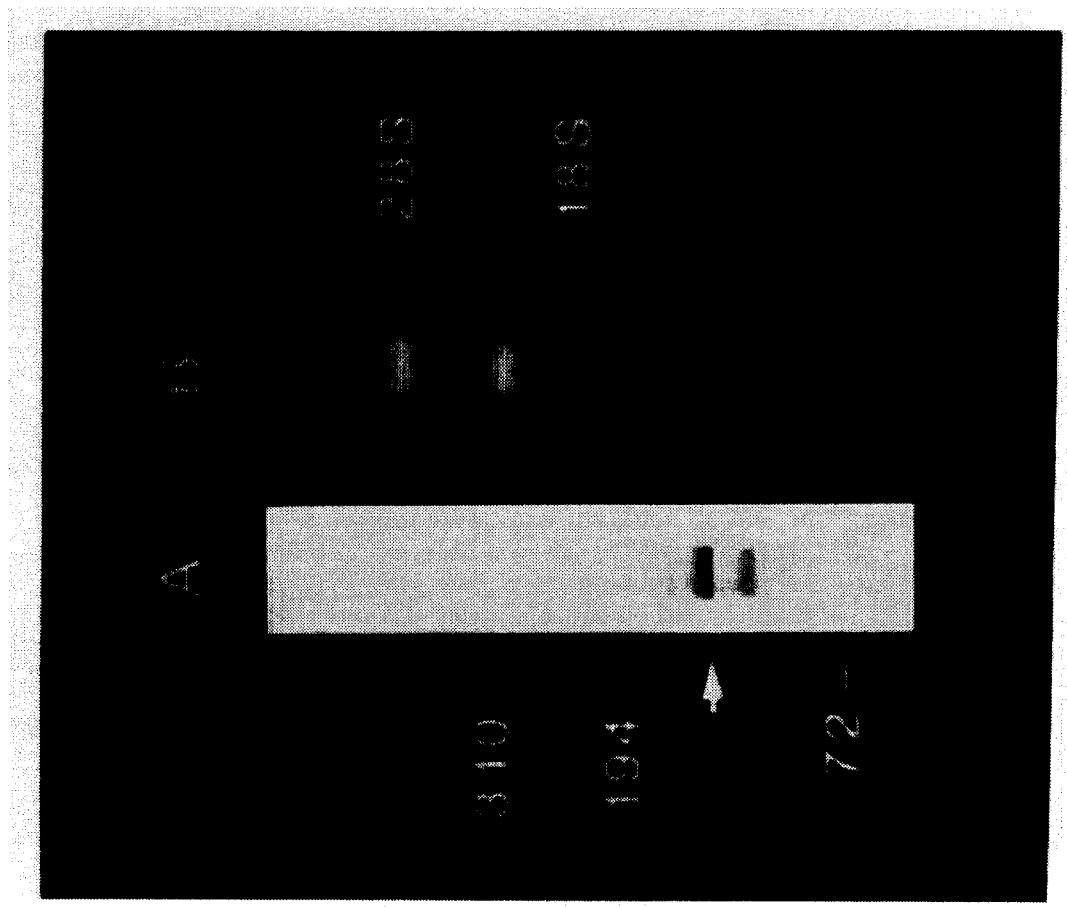
FIG. 3. Polyacrylamide gel analysis of the products of polymerase chain reaction (PCR) and Northern blot hybridization of the amplified clone to human insulinoma PNA. (A) 6% polyacrylamide gel electrophoresis of the products obtained following polymerase chain amplification of human insulinoma cDNA using the Asp and His primers described in Example 1 and 2. (Nishi et al., 1989) The position of the 150 bp band electroeluted and cloned (pPCR1) is indicated by the arrow. Size markers with HaeII-digested φX174 (BRL). (B) The cloned 150 bp band from (A) was PCR-labeled and used to probe human insulinoma poly(A)—selected RNA fractionated on a 1% agarose/formaldehyde gel. The position of ribosomal RNAs is indicated. Hybridization to insulinoma total RNA indicates that the higher molecular weight band does not correspond to 28s RNA.

Examination of a large number of proteolytic enzymes has shown that both the amino acid sequences surrounding the active site residues and the distance between the catalytic sites is highly conserved within any one family. In an effort to identify a mammalian gene homologous to the yeast KEX2 gene the inventors therefore designed two degenerate oligonucleotides based upon the consensus amino acid sequences surrounding the aspartate and histidine active site residues of kex2 and the related bacterial subtilisins. These oligonucleotides were used to prime polymerase chain amplification of cDNA synthesized from human insulinoma total RNA. Analysis of the PCR products by polyacrylamide gel electrophoresis revealed a major band of 150 nucleotides (FIG. 3). Because this was a length consistent with the distance between the Asp and His catalytic residues encoded by the KEX2 gene, the DNA was subcloned for further analysis. Sequencing of the cloned DNA (designated pPCR1) revealed that one of the two potential open reading frames displayed extensive amino acid sequence similarity to the corresponding region of the KEX2 gene. In addition, Northern blot analysis indicated the presence of both 5 and 2.8 kb transcripts in human insulinoma mRNA.

To isolate the corresponding full length cDNA clone, pPCR1 was used as a probe to screen a human insulinoma library. Screening of $10^6$ phage produced five positive signals which were plaque purified and subcloned. Sequence analysis of the longest insert, initially designated PC2, showed that it contained a single open reading frame of 1914 base pairs that was predicted to encode a 638 amino acid protein with an N-terminal signal peptide-like region (FIG. 4A, FIG. 4B and FIG. 4C). Translation of in vitro transcripts of PC2 in the reticulocyte cell-free system gave a protein band of the expected size of approximately 70 k dalton which was processed to a slightly smaller size in the presence of dog pancreas microsomes. This new protein was named convertin I.

The most salient feature of the predicted amino acid sequence of convertin I was the presence of a domain homologous to the subtilisin serine protease family (Table II, FIG. 5). As shown in FIG. 6, the amino acid sequences surrounding $Asp^{167}$, $His^{208}$, and $Ser^{384}$ of convertin I are closely related to the catalytic sites of both the bacterial subtilisins and the subtilisin-like yeast proteases KEX2 and proteaseB. In addition, the distances between these residues are consistent with those observed in proteases of the subtilisin family. A more thorough comparison of the similarities of convertin I with representative members of the subtilisin proteases indicated that strong homology existed throughout the active site domain. Computer analysis of the complete amino acid sequences of both convertin I and subtilisin BPN' generated only one region of extended overlap. This corresponds to the active site region in the subtilisin ($Gly^{20}$ to $Asp^{259}$) and extended from $Gly^{155}$ to $Asp^{424}$ in convertin I. Within this 246 amino acid segment, 27% of the residues were identical while 49% represented conservative substitutions. The strongest and most extensive similarities however, were evident when convertin I was compared to the yeast KEX2 protease. Alignment of these two sequences indicated that within a 282 amino acid overlap extending from $Asn^{122}$ to $Leu^{415}$ in convert in I, and asn to Leu in KEX2, 49% of the amino acids were identical. Moreover, 35% of the residues in this region were similar. (See Table I).

A comparison of the overall domain structures of convertin I and KEX2 is displayed in FIG. 7A and FIG. 7B. both proteins contain a putative signal peptide, followed by the 282 amino acid overlap that includes the subtilisin-like domain. Although this region contains the highest levels of homology between the two proteins, FIG. 7A and FIG. 7B shows that convertin I contains an amino acid sequence similarity with KEX2 throughout its sequence. Of the first 594 amino acids of convertin I, 34% are identical and 41% similar to those of the aligned KEX2 sequence. By comparison, 40–50% of the amino acids are identical between related mammalian members of the trypsin family of serine proteases (Hartley, 1970). The end of the similarity between convertin I and KEX2 is punctuated by the end of convertin I. Beyond this point, KEX2 contains a Ser/Thr-rich region followed by a transmembrane spanning domain. The former domain in KEX2 is thought to be involved in O-linked glycosylation of the protein (Fuller, et al., 1989). Both convertin I and kex2 (Mizuno, et al., 1984) possess consensus sequences for N-linked glycosylation. While analysis of convertin I indicates that it does not possess a transmembrane spanning domain, and therefore may not be associated with a membrane in vivo, it is of interest that Northern blot analysis of the human insulinoma RNA using either pPCR1 or convertin I as a probe, consistently demonstrated the presence of both 5 and 2.8 kb transcripts in these cells suggesting that an alternative form (perhaps membrane bound) of convertin may exist. Finally, both convertin I and kex2 (Fuller, et al., 1989; Mizuno, et al., 1988) possess highly charged, through otherwise unrelated, C-terminal tails. In convertin I 45% of the 38 carboxyl terminal amino acids are either acidic or basic residues. The charged tail in KEX2, which lies beyond the membrane-spanning region, is thought to be autoproteolytically removed during maturation of the protein (Fuller, et al., 1989).

A search of the NBRF-PIR protein sequence library revealed that convertin I was also related to the human furin gene product. Furin was identified based upon its proximity to the c-fes/fps proto-oncogene and is transcribed as a 4.5 kb mRNA (Roebroek, et al., 1988). Cloning and sequencing of 3.1 kb of the furin mRNA revealed a cystine-rich region with homology to the human insulin and growth factor receptors, as well as a transmembrane domain resembling those of the class I MHC antigens. Both of these domains are contained within the C-terminal half of the protein. Because the complete furin message has not been cloned, the nature of the amino-terminal region of this protein remains unknown. Interestingly, the similarity between furin and convertin I extends over the first 280 amino acids of the cloned furin fragment while spanning a 287 amino acid segment near the C-terminus of convertin I ($Asp^{310}$ to $Ser^{596}$). Within this region, 48% of the amino acids are identical. Likewise, the same region of furin shows 36% sequence identity with the corresponding region of kex2 ($Gly^{315}$ to $Ser^{597}$). Given these high levels of similarity, and the fact that this overlap includes a subtilisin-like serine active site region within furin that aligns to the putative active site serine residues of both convertin I ($Ser^{383}$) and KEX2 ($Ser^{385}$), the inventors infer that the uncharacterized amino-terminal portion of furin may also encode a subtilisin/KEX2-like catalytic domain.

The sequence of nucleic acid shown in FIG. 4A, FIG. 4B and FIG. 4C will find particular utility in the preparation of nucleic acid hybridization probes. These probes are useful in the identification and selection of recombinant clones bearing the desired sequence. To be useful hybridization probes must be a sufficient length to be able to form a relatively stable hybrid duplex with the target nucleic acid. Probes will also have to be prepared of a length to maximize duplex stability. Generally, such probes, whether DNA or RNA are about 14 or more nucleotides, preferably 18 or even 20. Minimum probe lengths are preferred in order to ensure stable duplex formation under the selected hybridization conditions. The use of such lengths also minimizes the possibility of cross-hybridization to unrelated sequences.

The practice of the present invention employs, unless otherwise indicated, molecular biological, microbiological and recombinant DNA techniques that are well known to the art. (See Maniatis, et al., 1982; Glover, 1985; Gait, 1984; Himes and Higgins, 1984; Press, 1986; and Perbal, 1984). DNA sequences that are substantially homologous can be identified in Southern hybridization experiments under conditions of select stringency. (See Maniatis).

Proinsulin has been recognized for 25 years. Many proteases have been proposed and rejected as the mammalian endoprotease which could cleave such prohormones to produce the active state. Attempts using methods of molecular biology have been unsuccessful for the past 5 years. Surprisingly, the inventors' strategy as described herein was successful in discovering a new mammalian protein, convertin I, different from all others previously reported in its structure and cleavage site. Using Northern blot analysis, this 70 kd protein has also been identified in rat insulinoma, rat pituitary, and rat brain.

One of the major advantages of the mammalian protein related to this invention is that it will be natural relative to mammalian molecules. Current use of, for example, trypsin to cleave recombinant human insulin (Lilly) generates side products requiring further purification. Use of the invention disclosed herein will correctly cleave more efficiently and, without side products. Allergic reactions will be reduced in comparison to use of non-human sources. Inactive hormones are less likely to be produced.

It is proposed generally that the invention disclosed herein will prove useful in screening clone banks from mammalian sources to detect other members of the family of proteins to which convertin I belongs, to cleave mammalian prohormones into active forms for commercial production of hormones by molecular genetic techniques, and to detect and investigate defects in preprocessing leading to various human diseases.

EXAMPLE 1

Polymerase Chain Reactions (PCR) and Amplification of Homologous DNA Fragments (AHF)

The degenerate nucleotide sequences of the primers used for PCR were derived from the amino acid sequences surrounding the aspartate and histidine active site residues of the yeast KEX2 gene and the bacterial subtilisins. The consensus amino acid and nucleotide sequences used for the aspartate site primer were:

```
        Ile                   Thr         Val
    Ala Ile  Val  Asp         Gly
    Ala                  Asp         Leu

CG   G   A    G     C    G    G G
    5'-      GC   AT   GT   GA   GA   GG    T - 3'
         TT   T   T    T    T    T    T T
``` and the histidine active site region and the corresponding complementary primer used were as follows:

```
    Asn                              Arg
        Tyr  His  Gly  Thr            Cys  Ala
    Asp                              His

G    G       G
    3'- TG  ATG  GTG  CC   TG  GT    ACG  CG - 5'
                  T    T       T
```

Reactions for PCR contained cDNA template, 100 pmol of each primer, and 2.5 units Taq DNA polymerase (Cetus) in 10 mM Tris (pH 8.3), 50 mM KCl, 1.5 mM $MgCl_2$, 0.2 mM dNTPs, 0.01% (w/v) gelatin in a volume of 0.1 ml. Reactions were carried out in a Perkin-Elmer-Cetus thermal cycler for 30 cycles of denaturation (94° C., 1 min), annealing (55° C., 2 min), and extension (72° C., 3 min). The cDNA templates for PCR were prepared from human insulinoma total RNA (5 µg) using Maloney murine leukemia virus (M-MLV) reverse transcriptase as suggested by the supplier (Bethesda Research Laboratories). One-fourth of the cDNA products of this reaction (1.25 µg equivalent of total RNA) was used for each PCR reaction. Following fractionation of the PCR products on a polyacrylamide gel, the band of interest was electroeluted and then amplified further by 15 cycles of PCR before being blunt-ended with T4 DNA polymerase and ligated into the EcoRV site of pBluescript (Stratagene) (see also Nishi et al., 1989).

EXAMPLE 2

Construction and Screening of the cDNA Library

Total RNA was isolated from human insulinoma using a modification of guanidinium isothiocyante, cesium trifluoroocetic acid (CsTFA) procedure (Example 5). Poly(A)$^+$ RNA was selected by oligo (dT)-cellulose chromatography using a commercial kit (5'→3'). Double-stranded cDNA was synthesized with a cDNA kit (Pharmacia LKB Biotechnology Inc.) followed by the addition of EcoRI adapters and cloning into the EcoRI site of gt10. One-half of the resulting library (complexity $2 \times 10^6$) was screened directly while the second half was amplified and stored. Duplicate filters were prepared, hybridized (2×SSC 37° C. for 18 h), and washed (2×SSC/0.1% sodium dodecye sulfate (SDS), 65° C. for 1 h) as described in Maniatis, et al. (1982). Following plaque purification, the cloned inserts were subcloned into the EcoRI site of pBluescript. To screen the library, labeled probe was prepared as follows: pPCR1 plasmid DNA (10 ng) was used as the DNA template for 30 cycles of PCR carried out as described above. This was followed by re-amplification of one-tenth (10 µl) of this reaction for 15 cycles in the presence of 0.2 mM d(ATP, GTP, TTP), 0.01 mM dCTP, and 25 µCi [$\alpha$-$^{32}$P] dCTP (3000 Ci/mmol) (DuPont, New England Nuclear).

EXAMPLE 3

Northern Blotting

RNA for Northern blots was fractionated on 1% agarose/formaldehyde gels. Following transfer to nitrocellulose, the blot was hybridized (2×SSPE, 50% formamide, 37° C. for 18 h) and washed (0.1×SSPE/0.1% sodium dodecye sulfate (SDS), 65° C. for 30 min) as described in Maniatis, et al. (1982).

EXAMPLE 4

DNA Sequencing

DNA sequencing was done by the dideoxy chain termination method using the Sequenase kit (United States Biochemical Corp.). Following sequencing from the T3 and T7 primer sites present in the pBluescript vector, the sequence information obtained was used to design new primers and the sequencing continued. This process was repeated until the insert was completely sequenced in both directions.

EXAMPLE 5

Guanidinium Isothiocyanate/CsTFA Method to Isolate Total RNA (Modification of Okayama, et al. 1987).

All solutions were prepared using autoclaved glassware or sterile disposable plasticware, autoclaved double-distilled water and chemicals of the finest grade. Solutions were sterilized by filtration through Nalgen 0.45 µm millipore filters and subsequently by autoclaving (except as noted). In general, treatment of solutions with diethyl pyrocarbonate was not carried out because residual diethyl pyrocarbonate may modify the RNA resulting in a marked reduction in its template activity.

REGENTS 5.5M GTC solution:

5.5M guanidine thiocyanate (Fluka or Eastman-Kodak), 25 mM sodium citrate, 0.5% sodium lauryl sarcosine. After the pH was adjusted to 7.0 with NaOH, the solution was filter-sterilized and stored at 4° C. Prior to use, 2-mercaptoethanol was added to a final concentration of 0.2M.

4M GTC solution:

The 5.5M solution shown above was diluted to 4M with sterile distilled water.

TE: 10 mM Tris-HCl (pH 7.5), 1 mM EDTA

PROCEDURE

Step 1, Extraction of Total RNA

Approximately $2-4\times10^8$ cells were treated with 100 ml of the 5.5M GTC solution. The viscous lysate was transferred to a sterile beaker, and the DNA was sheared by passing the lysate through a 16–18 gauge needle attached to a syringe several times until the viscosity decreases. After removal of cell debris by a brief low speed centrifugation, the lysate was gently overlaid onto a 17 ml cushion of CsTFA solution in autoclaved SW28 centrifuge tubes and centrifuged at 23,000 rpm for 24 hrs. at 15° C. After centrifugation, the upper GTC layer and the DNA band at the interface were removed by aspiration. The tubes were quickly inverted and their contents were poured into a beaker. Still inverted, they were placed on a paper towel to drain for 5 min. and then the bottom 2 cm of the tube was cut off with a razor blade or scalpel; the remainder was discarded. After the bottom of the tube is removed, the cup that was formed was turned over again and placed on a bed of ice. The RNA pellet dissolved in a total of 0.4 ml of the 4M GTC solution. After insoluble materials were removed by brief centrifugation in an Eppendorf microfuge, the RNA was precipitated as follows: 10 µl of 1M acetic acid and 300 µl of ethanol were added to the solution and chilled at −20° C. for at least 3 hours. The RNA was pelleted by centrifugation at 4° C. for 10 min. in a microfuge. The RNA pellet was dissolved in 1 ml of TE and the insoluble material was removed by centrifugation. One hundred µl of 2M NaCl and 3 ml of ethanol were added to the solution. The RNA was precipitated by centrifugation after chilling at −20° C. for several hours. The RNA was resuspended in water and stored at around −80° C.

EXAMPLE 6

Antiserum against convertin I

Various well-established, standard techniques are used to produce antiserum specific for a protein, in this example, convertin I: for use in routine immunofluorescence, radio-immunoassay, enzyme-linked immunosorbent assay (ELISA), Western blotting or immunoprecipitation combined with polyacrylamide gel electrophoresis. (Van de Ven et al., (1977); *Methods in Enzymology*, v. 104, Academic Press, Inc. (1984). As one example, convertin I is used as immunogen for two New Zealand White rabbits. Primary injections are made at multiple subcutaneous locations with 100 µg of purified protein, or of synthetic peptides corresponding to specific regions of the protein in complete Freund's adjuvant, and boosts with multiple injection of 50 µg in incomplete Freund's adjuvant at 2-week intervals. Peptide antigens are often coupled to a larger carrier protein to improve immunogenicity. After the first two boosts, subsequent boosts are made with protein or peptide conjugates. The animals are bled at the same time as booster injections are applied or at intervals of 10–14 days following the boosts. Substantial convertin I-specific immunoreactivity should be observed against purified protein after the fifth bleed, as measured by enzyme-linked immunosorbent assay (ELISA) or Western blotting. Antiserum used in immunoprecipitation can come from any bleed giving a sufficient titer: a suitable titer might be 10 to 20 µg of convertin I-specific immunoglobulin per milliliter of serum by ELISA.

Kits may be provided in accordance with the present invention to allow for detection of members of the convertin family either in clinical samples, tissues wherein processing of proteins is expected, or non-human mammals. Such kits would include a polyclonal or monoclonal Ab and an immunodetection reagent.

EXAMPLE 7

Synthetic Production of Convertins

In certain embodiments, convertins or segments thereof may be prepared in accordance with the invention by non-recombinant synthetic recons, e.g., by chemical synthesis or by use of a commercially available synthesizer, e.g., Applied Biosystems. This is usually only feasible for segments of about 40 amino acids. Due to practical limitation on the size of nucleotides that can readily be prepared synthetically, such chemical synthetic preparation techniques will likely find their greatest utility in the preparation of segments for use as hybridization probes.

For certain applications, e.g., where larger nucleic acid polymers are required, it may be advantageous to prepare suitable nucleic acid polymers by recombinant techniques. The most preferred approach is cDNA cloning in that a nucleic acid molecule is obtained having a transcription unit that does not require RNA splicing of the subsequent RNA transcript. This, of course, allows one to employ prokaryotic hosts for recombinant production of proteins. As is appreciated in the art, such hosts can not readily be employed to produce recombinant proteins where intron-containing coding sequences such as genomic sequences are used, due to the inability of the host to faithfully process the RNA intermediate.

EXAMPLE 8

Production and Use of Convertin I by Molecular Genetic Techniques

Suitable nucleic acid polymers may be prepared by recombinant techniques. The preferred approach is cDNA cloning (Example 1 and 2), in that a nucleic acid molecule is obtained having a transcription unit that does not require RNA splicing of the subsequent RNA transcript. This allows the use of a prokaryotic host for recombinant production of peptides. As is appreciated in the art, such hosts cannot readily be employed to produce recombinant peptides where intron-containing coding sequences such as genomic sequences are used due to the inability of the host to faithfully process the RNA intermediate.

Where recombinant techniques are employed to produce peptides in accordance with the invention, it will be appreciated by those skilled in the art in light of the present disclosure that it may be advantageous to prepare recombinant vectors such as plasmids, bacterial phage, viruses and so forth, which incorporate recombinant DNA sequences encoding the desired amino acid sequences of convertin I, or a biologically equivalent protein or peptide. The preparation and use of such vectors which incorporate the appropriate recombinant DNA segments will be apparent to those of skill in the art in light of the disclosure herein and in light of techniques well known in the art. As used herein, the term recombinant DNA segment or insert, means any DNA segment or fragment that is inserted into a recombinant vector either for the purpose of replicating or for expressing the recombinant fragment in a recombinant host to produce the desired peptide. Preparation and use of the recombinant DNA segments offers many advantages, including among others, the ability to construct DNA segments which include peptides having sequences which correspond generally to the endoprotease sequences disclosed herein (FIG. 4A, FIG. 4B and FIG. 4C), yet have sequence modification. This is referred to in the art as the ability to prepare so called second generation structures, for example, by site-specific mutagenesis.

Many gene transfer techniques are available to introduce genes into heterologous cells. One application is to transfer convertin along with neuroendocrine peptide genes. Two of the transfer methods used successfully for this purpose are: 1) those that achieve stable integration of the cloned genes into the genome of the heterologous cells; and 2) those that produce transient expression of the cloned genes. (Thomas, et al., 1988 have reviewed these approaches.)

In the "stable integration" method, the cloned DNA segment is engineered into a plasmid under the control either of its own or a heterologous promoter. The plasmid may be cotransfected into a cell population with a second plasmid containing a selectable marker, e.g., Tn5 aminoglycoside phosphotransferase (confers resistance to the antibiotic G418). Transfection methods are described in Gorman (1988); Gorman, et al. (1983). Not all cell types are amendable to these methods.

Radioimmunoassay or immunostaining procedures (well known to those skilled in the art) may be used to assay gene expression.

Alternative methods to achieve plasmid transfection employ defective, amphotrophic retroviruses. Higher transformation is possible with these methods than with those described above. Random incorporation into the genome leads to somewhat unpredictable results.

Transient gene expression systems employ the SV40 virus as a vector, e.g., (Gruss, et al. 1981). Efficiency of expression varies among mammalian cell types (Gorman, et al. 1982). There are size limits to the gene being transferred (Homen, et al. 1980). A specialized cell line (COS) may be used as an improvement to SV40 virus (Thomas, et al. 1988). This method has been successfully employed to express, e.g., rat and human preproinsulin.

Vaccinia virus genes are transcribed in infected cells without the incorporation of foreign splicing or transport signals. This vector is useful for inter-specific gene transfer and can transfer large foreign gene inserts. This method has successfully been employed to express processing endopepidase (e.g. KEX2) in mammalian cells. (Thomas, et al. 1988).

EXAMPLE 9

In Vitro Endoproteolytic Cleavage Assay

The in vitro endoproteolytic cleavage assay is carried out essentially as follows: $^{125}$I-labelled proinsulin is incubated with the protein, convertin I (obtained by translating the convertin I gene either in in vitro translation systems or in the in vivo *Xenopus* oocyte system) (*Methods in Enzymology,* 152, chaps. 28–30, 1987). Various recombinant vector methods can also be used to produce larger amounts of convertins (e.g., baculo virus, yeast, mammalian cells in culture) under various conditions, followed by treatment with carboxypeptidase B at pH8 for 5 minutes at room temperature. The products of these reactions are then analyzed by HPLC using a reverse phase C18 column and a 30–38% acetonitrile gradient developed over 1 hour. This system allows the determination of the site(s) and extent of endoproteolytic processing in proinsulin.

EXAMPLE 10

In Vivo Endoproteolytic Cleavage

Coinfection of mammalian cells with a recombinant vaccinia virus that expressed a mammalian neuroendocrine peptide precursor protein and a second vaccinia recombinant that contained the KEX2 gene will effect cleavage. (Thomas, et al. 1988).

EXAMPLE 11

Synthesis of Nucleic Acid Sequences

There are many methods well-known to those skilled in the art for synthesizing nucleic acid sequences. In the phosphotriester method, obligonucleotides are prepared and then linked to form longer segments (Narong, et al., 1979) as exemplified in the synthesis and cloning of the somatostatin gene (U.S. Pat. No. 4,356,270). The phosphodiester method of linking is also available (Brown, et al., 1979). Neither of these methods is very efficient in terms of time and labor, for large amounts.

Oligonucleotides may be synthesized using an automated DNA synthesis machine, e.g., that of Applied Biosystems, Inc., Foster City, Calif., which uses phosphoramidite chemistry (the manufacturer provides instructions).

EXAMPLE 12

Nucleic Acid Hybridization to Detect the Sequence Capable of Coding for Convertin I, or its Biologically Functional Equivalent The nucleic acid sequence information provided by the invention allows for the preparation of relatively short DNA (or RNA) sequences having the ability to specifically hybridize to gene sequences of the convertin I gene. In these aspects, nucleic acid probes of an appropriate length are prepared based on a consideration of the sequence shown in FIG. 4A, FIG. 4B and FIG. 4C. The ability of such nucleic acid probes to specifically hybridize to the convertin I gene sequences lend them particular utility in a variety of embodiments. Most importantly, the probes can be used in a variety of assays for detecting the presence of complementary sequences in a given sample. Other uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 14 base nucleotide stretches of the sequence shown in FIG. 4A, FIG. 4B and FIG. 4C. A size of at least 14 nucleotides in length helps to ensure that the fragment will be of sufficient length to form a duplex molecule that is both stable and selective. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production. Segments of from 18 to 22 bases are also within the scope of this invention.

Accordingly, the nucleotide sequences of the invention are important for their ability to selectively form duplex molecules with complementary stretches of the gene. Depending on the application envisioned, varying conditions of hybridization may be employed to achieve varying degree of selectivity of the probe toward the target sequence. For applications requiring a high degree of selectivity, relatively stringent conditions may be employed to form the hybrids, for example, selecting relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, preparation of mutants employing a mutant primer strand hybridized to an underlying template, or to isolate convertin I coding sequences from related species, functional equivalents, or the like, less stringent hybridization conditions are called for in order to allow formation of the heteroduplex. In these circumstances, conditions employed would be, e.g., such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, an enzyme tag such as urease, alkaline phosphatase or peroxidase, may be employed instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

One method of making molecules for detection of cell extracts is to use fluorescent probes. Fluorescent probes are well known to those skilled in the art. An example of a method is to bind fluorescein-labeled avidin (Vector Laboratories, Burlingame, Calif.) to a biotin-labeled protein. The signal may be enhanced.

EXAMPLE 13

Assay for Protease Activity and Ca Dependence (Mizuno, et al., 1987; 1988)

Protease activity is measured as follows: 20 mM of Boc-Gln-Arg-Arg-MCA, or other appropriate fluorogenic substrates, are incubated for one hour at 37° C. with the sample to be tested in buffer (various pH's: e.g., 0.1M sodium acetate pH5.5) containing 10 mM $CaCl_2$, pepstatin (1 mg/ml) and bestatin (1 mg/ml) in the presence or absence of 10 mM EGTA.

EXAMPLE 14

Computer Analysis

Computer analysis was done of the amino acid sequences of KEX2 and convertin I using any one of several commercially available software packages, e.g. LFASTA.

The NBRF-PIR protein sequence library was searched to reveal any other sequences related to convertin I.

EXAMPLE 15

Other Methods

Oligonucleotides for PCR and sequencing were synthesized on an Applied Biosystems model 380B DNA synthesizer. Unincorporated nucleotides were removed from PCR-labeling reactions by chromatography on NAP5 columns (Pharmacia). All other methods were as described in Maniatis et al., 1982; and Ausubel et al., 1988.

While the invention is susceptible to various modifications and alternative forms, specific embodiments thereof have been shown by way of example in the drawings and herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

The references listed below are incorporated herein by reference to the extent that they supplement, explain, provide a background for, or teach methodology, techniques, and/or compositions employed herein.

Reference 1. Adams, T. E., Alpert, S., and Hanahan, D., Nature, 325:223–228 (1987).
Reference 2. Andrews, P. C., Brayton, K. and Dixon, J. F., Experientia 43:784 (1987).
Reference 3. Ausabel et al., Current Protocals in Molecular Biology, V. 2, Wiley Interscience, N.Y. (1988).
Reference 4. Blobel, G., Dobberstein, B., J. Cell Biol. 67:835 and 852 (1975).
Reference 5. Brennan, S. O. and Peach, R. J., 229:167 (1988).
Reference 6. Brown et al., 1979.
Reference 7. Chan, S. J., Keim, P. and Steiner, D. F., Proc. Natl. Acad. Sci. U.S.A. 73:1964–1968 (1976).
Reference 8. Chick, W. L., Warren, S., Chute, R. N., et al., Proc. Natl. Acad. Sci. U.S.A., 74:628–632 (1977).
Reference 9. Davidson, H. W., Rhodes C. J., Hutton, J. C., Nature 333:93 (1988).
Reference 10. Dayoff, M. O. (ed) *Atlas of Protein Sequence and Structure*, 5, supp. 2, Nat'l Biomed. Res. Found., Georgetown Univ. p.3ff (1975).
Reference 11. Docherty, K. and Steiner, D. F., Ann. Rev. Physiol. 44:625 (1982).
Reference 12. Fletcher, et al., J. Cell Biol. 90:312 (1981).
Reference 13. Fuller, R. S., Brake, A. and Thorher, J., PNAS 86:1434 (1989).
Reference 14. Fuller, R. S., Brake, A. J. and Thorner, J., Science 246:482 (1989)
Reference 15. Fuller, R. S., Sterne, R. E., and Thorner, J., Ann. Rev. Physiol. 50:345 (1988)
Reference 16. Gait, M. J. (ed.), 1984.
Reference 17. Glover, D. N. (ed.), (1985).
Reference 18. Gorman, 1983, 1988, 1982.
Reference 19. Hastrup, S., Branner, S., Norris, et al., WO 89/06279 (1989).
Reference 20. Himes, B. H. and Higgins, S. J. (eds.), *Transcription and Translation*, 1984.
Reference 21. Homen et al., 1980.
Reference 22. Joliffe, et al., J. Bact. 141:1199 (1980).
Reference 23. Julius, D., Brake, A., Blair, L., Kunisawa, R., Thorner, J., Cell 37: 1075–89 (1984).
Reference 24. Julius, D., et al., Cell 32:839 (1983).
Reference 25. Kraut, J., Ann. Rev. Biochem. 46:331 (1977)
Reference 26. Kurjan, J., et al., Cell 30:933 (1982).
Reference 27. Loh, Y. P., Gainer, H., *Biosynthesis and processing of neuropeptides*, in *Brain Peptides*, Krieger, et al. (eas.), p. 79, Wiley and Sones, N.Y. (1983).
Reference 28. Loh, V. P., et al., J. Biol. Chem. 260:7194 (1983).
Reference 29. Loh, V. P., et al., PNAS (U.S.A.) 79:108 (1982).
Reference 30. Madsen, O. D., Andersen, C., Michelsen, B., et al., Proc. Natl. Acad. Sci. U.S.A. 85: 6652–6656 (1988).
Reference 31. Maniatis, T., Fritch, E. F., Sambrook, J. Cold Spring Harbor, N.Y. (1982).
Reference 32. Matsuo, H., Mizuno, K., U.S. Pat. No. 4,650, 763 (1987); U.S. Pat. No. 4,704,359 (1987).
Reference 33. Matsuo, H., Mizuno, K. and Takaharu, T., EPO 158 981 A2 (1985).
Reference 34. *Methods in Enzymology*, v. 104, Acad. Press., N.Y. (1984).
Reference 35. *Methods in Enzymology*, v. 152, chaps. 28–30, Berger and Kimmel (eds.) Acad. Press, N.Y., (1987).
Reference 36. Minth, C. D., Bloom, S. R., Polok, J. M., Dixon, J. F., PNAS (U.S.A.) 81:4377 (1984).
Reference 37. Minth, C. D., Bloom, S. R., et al., PNAS (U.S.A.) 81:4377 (1984).
Reference 38. Mizuno, K. et al., Nature 309: 558 (1984).
Reference 39. Mizuno, K., Nakamura, T., Ohshima, T., et al., Biochem and Biphys, Res. Comm. 156:246 (1988); 159: 305–311 (1989).
Reference 40. Moore, H. P., Waker, M. D., Lee, F. and Kelly, R. R., Cell 38:531–538 (1983).
Reference 41. Mullis, K. P., U.S. Pat. No. 4,683,202 (1987).
Reference 42. Narong et al., 1979.
Reference 43. Nishi, M., Chan, S. J., Nagamatsu, S., Bell, G. I., Steiner, D. F., PNAS (U.S.A.) 86:5738 (1989).
Reference 44. Noe, B. D., Debo, G., Spiess, I., J. Cell Biol. 99:578 (1984).
Reference 45. Oda, K. and Ikchuru, Y., J. Biochem. 104:159 (1988).
Reference 46. Okayama, H., Kawaichi, M., Brownstein, M., et al., Wil and Grossman (eds.) 154:3 (1987).
Reference 47. Orci, L., Ravassola, M., Amherdt, M., et al., *Direct Identification of Prohormone Conversion Site in Insulin-Secreting Cells*. Cell 42: 671–81 (1985).
Reference 48. Oshima, T., and Mizuno, K., EP 0 327 377 A2.
Reference 49. Perbal, *A Practical Guide to Molecular Cloning*, (1984).
Reference 50. Press, R. L., *Immobilized Cells and Enzymes*, (1986).
Reference 51. Rice, M. C., Wickner, W. T., *Mechanisms of membrane assembly and protein secretion in Escherichia coli*, in *Protein Transport and Secretion*, Gething (ed.), P. 44, Cold Spring Harbor Press (1985).
Reference 52. Roebroek, A. J. M., Schalker, J. A., Leunissin, J. A. M., et al., EMBO, 5:2197 (1986).
Reference 53. Sevarino, K. A., Stork, P., Ventimiglia, R., et al., Cell, 57:11–19 (1989).
Reference 54. Smeekens, S. P., and Steiner, D. F., J. of Hit. Chem. (Jn Press, 1990).
Reference 55. Steiner, D. F., Terris, S., Chan, S. J., et al. In: *Insulin and Islet Pathology—Islet Function and Insulin Treatment*, p. 55, ed. R. Luft Lindegren and Soner, Sweden (1976).
Reference 56. Stroud, R. M., Scient. Am. 13:74 (1974)
Reference 57. Steiner, D. F., Docherty, K., Chan, S. J., et al. In: *Biochemical and Clinical Aspects of Neuropeptides: Synthesis, Processing, and Gene Structure*, Acad. Press, Inc., pp 3–13 (1983).
Reference 58. Steiner, D. F., Bell, G. I., and Tager, H. S., Chap 75 In: *Endocrinology*, L. DeGroot (ed.) W. B. Saunders, pp. 1263–1289 (1989).
Reference 59. Thim, L., et al., PNAS (U.S.A.) 83:6766 (1986).

Reference 60. Thomas, G., Thorne, B. A., and Hruby, D. E., Ann. Rev. Physiol. 50:323 (1988).
Reference 61. Van de Ven, W. J. M., Roebroek, A. J. M., Scholken, J. A., EPO 246 709 A1.
Reference 62. Van de Ven, W. J. M, *Virology* 8:334 (1977).
Reference 63. Wells, J. A., Cunningham, B. C., Graycar, and Estell, D. A., Trans. R. Soc. Land. A317: 415 (1986).
Reference 64. Wells, J. A., Ferrari, E., Henner, D. J., et al., Nucl. Acid Res. 11:7911–7925 (1983).
Reference 65. White, Handler, Smith, *Principles of Biochemistry*, 5th Ed. McGraw-Hill Book Co., N.Y., pp. 271–272 (1973).
Reference 60. Wickner, R. B. and Liebowitz, M. J., Genetics 82: 429–442 (1976).
Reference 61. Zurowski, M. M., Stabinsky, Y. and Levitt, M., WO 88/08033 (1988).

What is claimed is:

1. An isolated nucleic acid segment having a nucleotide sequence coding for mammalian convertin wherein:

the encoded convertin comprises an amino acid sequence as set forth in FIG. 4.

2. A recombinant vector incorporating a nucleic acid segment in accordance with claim 1.

3. The vector of claim 2 further comprising a promoter.

4. The vector of claim 3, wherein the promoter is further defined as a eukaryotic promoter.

5. The vector of claim 3, wherein the promoter is further defined as an SV40, CMV, or rat insulin promoter.

6. A recombinant host cell incorporating the nucleic acid segment of claim 1.

7. The host cell of claim 6 wherein the nucleic acid segment is part of an integrated recombinant vector.

8. The host cell of claim 6 wherein the nucleic acid segment is a DNA segment which is part of a transcriptional unit.

9. The host cell of claim 8 wherein the transcriptional unit is positioned adjacent to and under the control of a promotor.

10. The host cell of claim 9 wherein the promoter is a eukaryotic promoter and the transcriptional unit includes polyadenylation signal.

11. The host cell of claim 6 further defined as a eukaryotic cell.

12. A nucleic acid segment of 14–22 bases having a nucleotide sequence which specifically hybridizes with the nucleic acid sequence of FIG. 4, or its complement.

13. The nucleic acid segment of claim 12 further defined as a DNA segment.

14. A method of detecting the nucleic acid of claim 1 in a biological sample, said method comprising the following steps:

(a) preparing a nucleotide probe in accordance with claim 12;

(b) incubating the probe with the biological sample to be tested under selective conditions appropriate for the formation of specific hybrids; and (c) detecting the formation of specific hybrids between the probe and the nucleic acid of the biological sample, the formation of such hybrids being indicative of the presence of the nucleic acid.

15. The method of claim 14 wherein the probe is labelled.

16. The method of claim 15 wherein the probe is labelled with a fluorescent labels.

* * * * *

UNITED STATES PATENT AND TRADEMARK OFFICE
CERTIFICATE OF CORRECTION

PATENT NO. : 5,541,062

DATED : July, 30, 1996

INVENTOR(S) : Smeekens et al.

It is certified that error appears in the above-identified patent and that said Letters Patent is hereby corrected as shown below:

```
In claim 16, column 30, line 30, delete "labels", and insert
 --label-- therefor.
```

Signed and Sealed this

Twelfth Day of November, 1996

Attest:

BRUCE LEHMAN

*Attesting Officer*   *Commissioner of Patents and Trademarks*